(12) United States Patent
Hanak et al.

(10) Patent No.: US 6,743,780 B1
(45) Date of Patent: Jun. 1, 2004

(54) PLASMID STABILIZATION

(75) Inventors: Julian A. J. Hanak, Macclesfield (GB); Steven G. Williams, Near Crewe (GB); Scott D. Gorman, Witney (GB); David J. Sherratt, Witney (GB)

(73) Assignee: Cobra Biologics Limited, Newcastle (GB)

( * ) Notice: Subject to any disclaimer, the term of this patent is extended or adjusted under 35 U.S.C. 154(b) by 0 days.

(21) Appl. No.: 09/439,008

(22) Filed: Nov. 12, 1999

Related U.S. Application Data

(63) Continuation of application No. 09/079,792, filed on May 15, 1998, now abandoned, which is a continuation-in-part of application No. 08/988,996, filed on Dec. 11, 1997, now abandoned, which is a continuation of application No. 08/708,921, filed on Sep. 6, 1996, now abandoned

(60) Provisional application No. 60/004,271, filed on Sep. 25, 1995.

(30) Foreign Application Priority Data

Sep. 8, 1995 (GB) .............................................. 9518395
Sep. 6, 1996 (WO) .............................. PCT/GB96/02208

(51) Int. Cl.⁷ .......................... C12Q 1/68; A61K 48/00
(52) U.S. Cl. ............................. 514/44; 435/6; 435/325; 435/375; 435/41; 536/24.1
(58) Field of Search ...................... 514/44; 435/7.2, 435/71.1, 71.2, 320.1, 325, 252.3, 254.2

(56) References Cited

U.S. PATENT DOCUMENTS

| | | |
|---|---|---|
| 4,920,048 A | 4/1990 | Diderichsen |
| 5,015,573 A | 5/1991 | Yarranton et al. |
| 5,763,270 A | 6/1998 | Eastman et al. |
| 6,103,470 A | 8/2000 | Eastman et al. |

FOREIGN PATENT DOCUMENTS

| | | |
|---|---|---|
| EP | 0 106 542 | 4/1984 |
| WO | WO 94/02609 | 2/1994 |

OTHER PUBLICATIONS

Pedersen EA, 2001 Encyclopedia of Life Sciences (Nature Publishing group/www.els.com) 1–8.*

Human gene therapy : W. French Anderson ; Nature vol. 392 pp. 25–30.*

Brossier, Fabien, et al., "Protective Antigen–Mediated Antibody Response against a Heterologous Protein Produced in Vivo by *Bacillus anthracis*," *Infection and Immunity*, 68(10):5731–5734, (2000).

Cranenburgh, Rocky M, et al., "*Escherichia coli* strains that allow antibiotic–free plasmid selection and maintenance by repressor titration," *Nucleic Acids Research*, 29(5):1–6, (2001).

Curtiss, Roy, III, "Bacterial Infectious disease control by vaccine development," *The Journal of Clinical Investigation*, 110(8):1061–1066, (2002).

(List continued on next page.)

Primary Examiner—Andrew Wang
Assistant Examiner—James Douglas Schultz
(74) Attorney, Agent, or Firm—Cozen O'Connor, P.C.

(57) ABSTRACT

A system is described which utilizes a novel system of repressor titration for maintenance of a plasmid useful in gene therapy and production of a recombinant protein. The system utilizes a transformed host cell containing a plasmid including an operator susceptible to binding by a repressor expressed in trans, a first chromosomal gene encoding the repressor, and a second chromosomal gene that is functionally associated with an operator and essential for cell growth, wherein the plasmid is present in the cell in sufficient numbers to titrate the repressor such that the essential gene is expressed, thereby permitting cell growth.

7 Claims, 4 Drawing Sheets

OTHER PUBLICATIONS

Galen, James E., et al., "Optimization of Plasmid Maintenance in the Attenuated Live Vector Vaccine Strain *Salmonella typhi* CVD 908–htrAt," *Infection and Immunity*, 67(12):6424–6433, (1999).

Gossen et al., "Control of gene activity in higher eukaryotic cells by prokaryotic regulatory elements," *TIBS*, 18:471–475, (1993).

Hanahan, Douglas, et al., "Plasmid Transformation of *Escherichia coli*," *Methods in Enzymology*, 204:63–113, (1991).

Hoiseth, Susan K. and Stocker, B. A. D., "Aromatic–dependent *Salmonella typhimurium* are non–virulent and effective as live vaccines," *Nature*, 291:238–239 (1981).

Kang, Ho, Young, et al., "Immune Responses to Recombinant Pneumococcal PspA Antigen Delivered by Live Attenuated *Salmonella enterica* Serovar Typhimurium Vaccine," *Infection and Immunity*, 70(4):1739–1749, (2002).

Kremer, Laurent, et al., "Systemic and Mucosal Immune Responses after Intranasal Administration of Recombinant *Mycobacterium bovis* Bacillus Calmette–Guerlin Expressing Glutathione S–Transferase from *Schistosoma haematobium*," *Infection and Immunity*, 66(12):5669–5676, (1998).

Lebedeva et al., "A new T7 RNA polymerase–driven expression system induced via thermoamplification of a recombinant plasmid carrying a T7 promoter–*Escherichia coli* lac operator," *Gene*, 142:61–66, (1994).

Levine, Myron M. and Noriega, Fernando, "A review of the current status of enteric vaccines," *PNG Med. J.*, 38:325–331, (1995).

Noriega, Federnando, R., et al., "Further Characterization of ΔaroA ΔvirG *Shigella flexnari* 2a Strain CVD 1203 as a Mucosal Shigella Vaccine and as a Live–Vector Vaccine for Delviering Antigens of Enterotoxigenic *Eschierichia coli*," *Infection and Immunity*, 64(1):23–27, (1996).

Ryan, Edward T., et al., "Development of ΔglnA Balanced Lethal Plasmid System for Expression of Heterologous Antigens by Attenuated Vaccine Vector Strains of *Vibrio cholerae*," *Infection and Immunity*, 68(1):221–226, (2000).

Soussi, Neirouz, et al., "*Listeria monocytogenes* as a Short–Lived Delivery System for the Induction of Type 1 Cell–Mediated Immunity against the p36/LACK Antigen of *Leishmania major*," *Infection and Immunity*, 68(3):1498–1506, (2000).

Tacket, Carol O., et al., "Safety and Immunogenicity in Humans of an Attenuated *Salmonella typhi* Vaccine Vector Strain Expressing Plasmid–Encoded Hepatitis B Antigens Stabilized by the Asd–Balanced Lethal Vector System," *Infection and Immunity*, 65(8):3381–3385, (1997).

Theys, J., et al., "Clostridium as a tumor–specific delivery system of therapeutic proteins," *Cancer Detect Prev.*, 25(6):548–557, (2001) (Abstract), Abstract considered.

Titball, Richard W., et al., "Expression of the *Yorsinia pestis* Capsular Antigen (F1 Antigen) on the Surface of an aroA Mutant of *Salmonella typhimurium* Induces High Levels of Protection against Plague," *Infection and Immunity*, 65(5):1926–1930, (1997).

Williams, Steven G., et al., "Repressor titration: a novel system for selection and stable maintenance of recombinant plasmids," *Nucleic Acids Research*, 26(9):2120–2124, (1998).

\* cited by examiner

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 1:

CGGNNNNNWN NNNNCCG

-continued (2) INFORMATION FOR SEQ ID NO: 2:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 2:

GGAATTGTGA GCGGATAACA ATT                         23

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO: 3:

GGAATTGTGA GCGGATAACA ATTTCCCG                  28

PLASMID STABILIZATION

This is a continuation of U.S. application Ser. No. 09/079,792, filed on May 15, 1998 now abandoned, which is a continuation-in-part of U.S. application Ser. No. 08/988,996, filed on Dec. 11, 1997, which is abandoned, which is a continuation of U.S. application Ser. No. 08/708,921, filed on Sep. 6, 1996 now abandoned, and claims priority benefit of International Application No. PCT/GB96/02208, filed on Sep. 6, 1996 and U.S. Provisional Application Serial No.60/004,271, filed on Sep. 25, 1995, and GBRI Application Serial No.9518395.0, filed on Sep. 8, 1995, all applications incorporated by reference herein in their entireties.

FIELD OF THE INVENTION

The invention relates in general to stable maintenance of a plasmid, and in particular to that of a plasmid containing a gene useful in gene therapy.

BACKGROUND OF THE INVENTION

The stable maintenance of a plasmid, particularly at high copy number, is important for the preparation of plasmid DNA. However, extrachromosomal DNA carried in host cells is inherently unstable in cell culture because cultured cells which contain plasmids usually have an increased metabolic burden compared to plasmid-free segregant cells. In efforts to maintain plasmid stability and decrease metabolic burden, plasmids engineered to contain dominant selectable markers have been routinely used. During scale-up fermentation of bacterial or yeast host strains, the presence of the selecting agent prevents plasmid loss and overgrowth by cells not burdened by the effort of replication and maintenance of plasmid DNA.

Antibiotic resistance genes, for example encoding resistance to antibiotics such as ampicillin, kanamycin or tetracycline, are the most common dominant selectable markers used in molecular biology cloning and fermentation procedures for the production of recombinant proteins or plasmid DNA. For continuous fermentation in the presence of an antibiotic, selective pressure is lost because the antibiotic loses activity over time due to culture dilution or degradation by the host cell. Therefore, some of the more successful methods for maintaining plasmids do not utilize antibiotic selection but rather rely on a mutant host which is unable to synthesize an amino acid, inserting the gene which provides for this synthesis in the plasmid. Other solutions which prevent the takeover of a culture by plasmid-free segregant involve placing a gene coding for a toxic product in the chromosome and then including a corresponding repressor system in the plasmid. Plasmid-free cells are effectively killed upon segregation.

Even with selective pressure, however, plasmid-free cells may continue to grow due to leakage of the complementing product of the selective gene from plasmid-bearing cells, lowering the total plasmid productivity of the culture. In addition, the use of genes for antibiotic resistance or other dominant selectable markers on vectors intended for gene therapy has raised potential problems related to expression of those genes in the target mammalian cell or host mammalian organism. Promiscuous expression of plasmid-borne genes, such as drug-resistance or nutritional markers, of the host cell (e.g. a yeast or bacteria) in the target mammalian cell may lead to its destruction and/or to an antigenic response to the gene product in the mammal. There are also concerns regarding contamination of the final product with the antibiotic used for plasmid selection in culture, with the potential induction of a severe immune response to the antibiotic, e.g., anaphylactic shock. The widespread use of bacterial genes for antibiotic resistance also will ultimately result in their transfer to the bacterial population as a whole.

The stable maintenance of plasmids at high copy number in transfected cells is also of importance in ex vivo gene therapy. Following the administration of a transfected cell, such as a microorganism or other cell, to a recipient organism (e.g., a mammal) for therapy, it becomes difficult or impossible to maintain plasmid DNA within the transplanted cells because it is difficult to select for a plasmid in vivo. For example, use of the in vitro selection compound may be contraindicated in the recipient, as would be the deletion of a given biochemical constituent (such as an amino acid) from the enviroment surrounding the transplanted cells, were such a feat of biological engineering as the latter technically feasible. As is true for in vivo nucleic acid delivery methods, it is advantageous to remove from the plasmids bearing the therapeutic- or other gene of interest genes that are not relevant to the therapeutic application, in order to minimize potential risks stemming from transmission of their products to the recipient, which may provoke side effects such as a toxic or anaphylactic response.

There is, therefore, a need for a method of plasmid maintenance that does not require the presence of extraneous plasmid-borne host genes or antibiotic selection.

SUMMARY OF THE INVENTION

The invention encompasses a transformed host cell containing a plasmid comprising an operator susceptible to binding by a repressor expressed in trans, a first chromosomal gene encoding the repressor, and a second chromosomal gene that is functionally associated with an operator and essential for cell growth, wherein the plasmid is present in the cell in sufficient numbers to titrate the repressor such that the essential gene is expressed, thereby permitting cell growth.

As used herein, "functionally associated" or "operatively associated", with respect to an operator sequence and an associated gene, means that the operator is linked in cis to the gene such that expression of the gene is susceptible to repression upon binding of a repressor to the operator. It will be understood by one of skill in the art that the operator sequence present on the plasmid need not be a sequence that is identical to the operator sequence on the chromosomal gene, in that the plasmid operator need only consist of the minimal sequences necessary for binding the repressor that represses transcription of the chromosomal gene. It will also be understood that mutated operator sequences are also useful according to the invention, for example, sequences having one or more nucleotides inserted, deleted, or substituted which result in increased or decreased affinity for the corresponding repressor. As used herein, "cell growth" refers to increasing numbers of cells in a culture medium over time, and also refers to cell survival where the number of cells does not increase over time, but rather the number of live cells does not decrease over time.

Preferably, the repressor gene encodes one of the lac repressor, the λ repressor, the *E. coli* trp repressor, the *E. coli* galR repressor, and the *E. coli* araC repressor. As described above, each repressor is operative in trans with a trans-associated operator sequence that is present both in the chromosome and on the plasmid. The invention contemplates the presence of one or more repressor genes on the host chromosome, e.g., one, two or three repressor genes, in order to ensure plasmid stability where one chromosomal repressor gene becomes mutated or deleted.

Preferred operator sequences therefore include the lac operator, the λ operator, the trp operator, the gal operator, and the ara operator. If desired, the corresponding promoter may be functionally associated with its operator. Note that bacterial repressor/operator systems are of use in yeast including, but not limited to, the Lac repressor/operator pair, which may be used to block access of positive regulators of yeast transcription to their respective binding sites (e.g. the binding of Gal4p to the sequence $CGGN_5(A/T)N_5CCG$ [SEQ ID NO: 1].

In other preferred embodiments, the cell is a bacterial cell that may be either gram negative or positive, for example, *E. coli*, Listeria, Shigella, Clostridium, Salmonella, Bacillus or Lactococcus. Alternatively, the host cell may be a yeast, mycobacterial, slime mold, algal or fungal cell, or other cell of the Domain Arachaea (including archaebacteria), phylum Protista, or animal or plant kingdom.

More than one different essential chromosomal gene may be present in the cell chromosome, wherein two or more essential genes are linked to an operator and are therefore susceptible to repression by the repressor; in this way, accidental de-repression of a single essential gene (e.g. through mutation of its associated operator) cannot result in the growth of plasmid-free cells, since at least one other essential gene remains repressed. In one preferred embodiment of the invention, the gene encoding the repressor protein is present in two or three copies at different locations in the chromosome to guard against loss of repressor expression at one chromosomal location. It is also contemplated that a single essential gene may be operatively linked to more than one operator sequence, such that a mutation in any one such element will be insufficient to de-repress transcription of the gene.

Preferred essential genes that are located on the host chromosome include but are not limited to genes falling within the following categories: genes encoding products related to the biosynthesis of cell metabolites, genes whose products are involved in carbon metabolism, genes coding for antibiotic resistance, and genes encoding biosynthesis or regulation of macromolecules, e.g., genes essential for DNA and/or RNA synthesis and replication functions.

In preferred embodiments, the plasmid comprises an origin of replication permitting replication of about 10–50 copies, 40–200 or 100–200 copies of the plasmid per host cell.

Examples of such plasmids include, but are not limited to, bacterial plasmids pBR322, pUC, pHETK, pT181, pMB1, pNZ2123 and pIL253, and yeast plasmids YRp and YEp.

It is preferred that the plasmid comprises a cloning site for insertion of a gene of interest.

In one especially preferred embodiment of the invention, the plasmid further comprises a gene of interest operatively associated with control sequences for expression in a mammalian, preferably a human, cell. Examples of such genes are known in the art and disclosed herein. If desired, the gene of interest will not have a host cell promoter and therefore will not be expressed in the host cell. In addition, if desired, the gene of interest may be associated with the plasmid operator sequence such that expression of this gene is repressible upon growth of the plasmid-transformed host cell. These serve to reduce the metabolic burden to the host cell of producing the encoded protein of interest. Alternatively, if expression of the gene of interest is desired, e.g., where it is desirable to produce and isolate the encoded product, the operator need not be positioned so as to repress expression of the gene of interest upon cell growth and expression of the gene of interest may be driven by a host cell promoter.

As used herein, the terms "mammalian" or "mammal" refer to any member of the class Mammalia, including a human.

Preferably, the plasmid consists essentially of an operator susceptible to binding by a repressor, an origin of replication, and a cloning site for insertion of a gene of interest.

As used herein, "consists essentially of" means that the plasmid contains only those sequences necessary for maintaining the plasmid in the host strain, and a cloning site for insertion of a gene of interest. That is, the plasmid does not contain sequences that are unnecessary to its survival in the host (e.g., bacterial, yeast or other) strain.

As used herein, "origin of replication" refers to those sequences on the plasmid that are necessary for maintaining the plasmid at a given copy number per host cell.

Preferably, the plasmid is about 1000 bp in length.

It is also preferred that the plasmid is about 2,500 bp in length.

In another preferred embodiment, the plasmid is about 5,000 bp in length.

In another aspect, the invention provides a plasmid such as that described above, e.g., consisting essentially of an operator susceptible to binding by a repressor, an origin of replication, and a cloning site for insertion of a gene of interest. It is contemplated that the DNA contained in the plasmid that is other than the operator sequence, the origin of replication, and the cloning site is non-coding DNA.

Preferably, the plasmid further comprises a said gene of interest cloned into said cloning site, particularly a gene of interest operatively associated with control sequences for expression in a mammalian, preferably a human, cell.

The minimal plasmid possesses the considerable advantage of containing only minimal bacterial DNA sequences, and thus considerably reduces the problems associated with the introduction of bacterial DNA sequences into mammalian cell lines, for example, where a plasmid is intended as a vector for gene therapy. Thus, problems that are avoided according to the invention include expression of plasmid-borne bacterial, yeast or other host genes in a mammalian target cell which lead to destruction of the target cell or the mammalian host itself, or which lead to development of an immune response to the foreign DNA or to products encoded by such sequences.

The invention also provides a method of maintaining a plasmid in a host cell, comprising the step of culturing a cell containing a plasmid comprising an operator susceptible to binding by a repressor, a first chromosomal gene encoding the repressor, and a second chromosomal gene that is functionally associated with the operator and is essential for cell growth, wherein the plasmid is present in the cell in sufficient numbers to titrate the repressor such that the essential gene is expressed, thereby permitting cell growth, for a time and under conditions sufficient to permit the cell to grow.

Another aspect of the present invention is a method of producing plasmid DNA, comprising culturing a cell comprising a first chromosomal gene encoding a repressor, a second chromosomal gene that is functionally associated with an operator susceptible to binding by the repressor and is essential for cell growth, and a plasmid comprising the operator, wherein the plasmid is present in the cell in sufficient numbers to titrate the repressor such that the essential gene is expressed, thereby permitting cell growth, for a time and under conditions sufficient to permit the cell to grow, and isolating plasmid DNA from the cell.

Preferably, the plasmid further comprises a gene encoding a recombinant protein, which gene is functionally linked to sequences which cause the gene to be expressed in a mammalian cell, e.g. a human cell.

The invention additionally encompasses a method of producing a recombinant protein, comprising culturing a cell containing comprising a first chromosomal gene encoding a repressor, a second chromosomal gene that is functionally associated with an operator susceptible to binding by the repressor and is essential for cell growth, and a plasmid comprising the operator and a gene encoding a recombinant protein, which gene is expressed in the cell, wherein the plasmid is present in the cell in sufficient numbers to titrate the repressor such that the essential gene is expressed, thereby permitting cell growth, for a time and under conditions sufficient to permit the cell to grow, and isolating the recombinant protein from the cell.

It is contemplated that the recombinant protein is a protein of therapeutic benefit to a human.

Production of a recombinant protein using the repressor titration system described herein confers a reduced metabolic burden on the host cell in that the only coding region on the plasmid is the gene encoding the recombinant protein. Therefore, the host cell need not support production of plasmid-encoded proteins other than the recombinant protein.

The repressor titration system described herein enables the stable maintenance of plasmids in moderate or high copy number without the use of plasmid-encoded dominant selectable markers, such as for antibiotic resistance, and can be used with any host that can support a trans-acting repressor/operator system. One advantage of the invention is in its reliance on plasmid maintenance other than by antibiotic selection of plasmid-bearing cells. That is, there is no loss of selective pressure during fermentation due to loss of activity of an antibiotic. The absence of dominant selectable markers, such as antibiotic resistance genes or nutritional markers, on the plasmid, as described herein, is also advantageous in that it avoids the potentially serious problems related to expression of those genes in the target mammalian cell. The invention thus also avoids contamination of a product intended for gene therapy with the antibiotic used for selection of the gene therapy vector. In addition, the invention avoids the potential induction of a severe immune response to such antibiotics, e.g., anaphylactic shock.

One considerable advantage to the non-antibiotic plasmid selection system described herein is that it avoids widespread use of bacterial genes encoding antibiotic resistance, which use tends to promote transfer of such genes in the bacterial population as a whole.

Another aspect of the present invention is a method of delivering a stably-maintained plasmid to a recipient organism, comprising culturing a cell comprising a first chromosomal gene encoding a repressor, a second chromosomal gene that is functionally associated with an operator susceptible to binding by the repressor and is essential for cell growth, and a plasmid comprising the operator, wherein the plasmid is present in the cell in sufficient numbers to titrate the repressor such that the essential gene is expressed, thereby permitting cell growth, for a time and under conditions sufficient to permit the cell to grow, and transplanting the cell to the recipient organism under conditions sufficient to permit the cell containing the plasmid to be present in the recipient organism after being so transplanted.

As used herein, the term "organism" refers to all multicellular life-forms; such organisms may provide cells which may serve as host cells for a plasmid of the invention or may serve as recipients of a transformed host cell of the invention. Organisms that are of particular use as host-cell recipients are mammals.

In contrast, the term "microorganism" refers to any unicellular organism. Microorganisms are of use in the invention as plasmid host cells, and include (but are not limited to) yeast, bacteria, members of the Domain Arachaea and the phylum Protista, slime molds, unicellular fungi and algae Preferably, the cell is a yeast cell.

In another preferred embodiment, the cell is a bacterial cell.

It is preferred that the transplanting comprises injection of the cell into the recipient organism.

The invention also provides a method of maintaining a host cell containing an exogenous DNA in a host organism, comprising the steps of culturing a cell comprising a first chromosomal gene encoding a repressor, a second chromosomal gene that is functionally associated with an operator susceptible to binding by the repressor and is essential for cell growth, and a plasmid comprising the operator and a gene of interest which is expressed in the cell, wherein the plasmid is present in the cell in sufficient numbers to titrate the repressor such that the essential gene is expressed, thereby permitting cell growth, for a time and under conditions sufficient to permit the cell to grow, and transplanting the cell to the recipient organism under conditions sufficient to permit the cell to produce a product encoded by the gene of interest in the organism, wherein the cell containing the plasmid is present in the organism after being so transplanted. A final aspect of the present invention is a pharmaceutical composition comprising a cell comprising a first chromosomal gene encoding a repressor, a second chromosomal gene that is functionally associated with an operator susceptible to binding by the repressor and is essential for cell growth, and a plasmid comprising the operator and a therapeutic gene which is expressed in the cell, wherein the plasmid is present in the cell in sufficient numbers to titrate the repressor such that the essential gene is expressed, thereby permitting cell growth, and a pharmaceutically-acceptable carrier.

Pharmaceutically-acceptable carriers of use in the invention include, but are not limited to, aqueous solutions, such as physiological buffers (e.g. saline), cell culture media, or other excipients or adjuvants as are known in the art, as well as body fluids (e.g. blood or lymphatic fluid) from the recipient organism. A pharmacologically-acceptable carrier may additionally be selected from hydrogel materials that include, but are not limited to, non-fibrogenic alginate, agarose, alginic acid, carrageenan, collagen, gelatin, polyvinyl alcohol, poly(2-hydroxyethyl methacrylate), poly(N-vinyl-2-pyrrolidone) or gellan gum, either alone or in combination, or, alternatively, liquid, gelled, polymeric, co-polymeric or particulate formulations of aminated glucopolysachharides.

Other features and advantages of the invention will be apparent from the following description of the preferred embodiment thereof and from the claims.

DESCRIPTION

The invention is based on the discovery of a plasmid maintenance system which does not require the use of a plasmid-borne dominant selectable marker, but rather utilizes a novel system of repressor titration.

The invention is illustrated by the following nonlimiting examples wherein the following materials and methods are employed. The entire disclosure of each of the literature references cited hereinafter are incorporated by reference herein.

Figure 1:
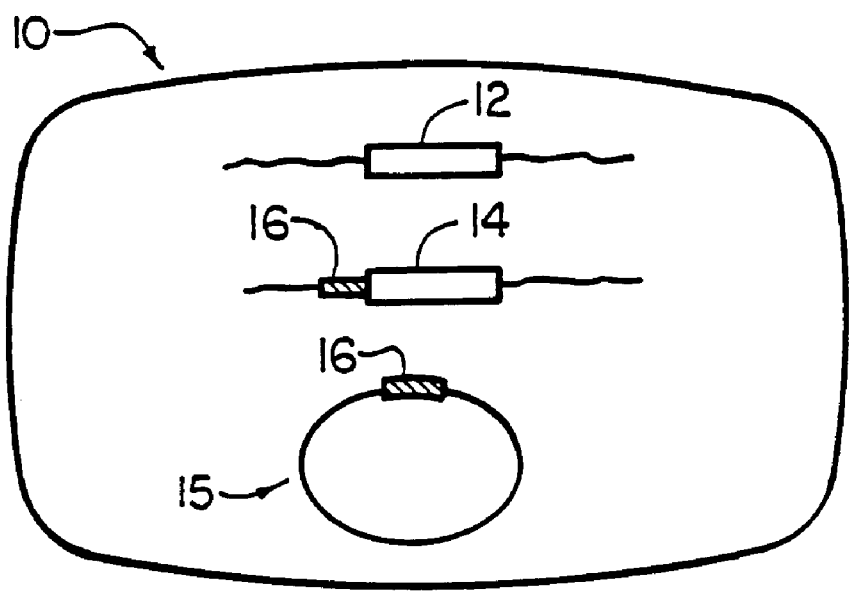
FIG. 1 is a schematic drawing of a plasmid-transformed host cell according to the invention.
Figure 2:
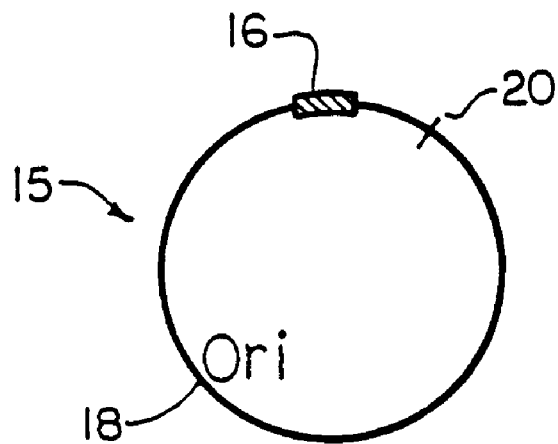
FIG. 2 is a schematic drawing of a minimal plasmid according to the invention.

The invention is based on transformed host cells, plasmids, and methods for improved production and maintenance of a plasmid in a host cell using a novel system of repressor titration (FIG. 1). Plasmid DNA produced according to the invention is useful in gene therapy. The plasmid itself may consist of certain minimal sequences, as shown in FIG. 2, and is capable of carrying a therapeutic gene of interest. The novel repressor titration system works as follows:

The system, as presented in FIGS. 1 and 2, utilizes a host cell 10 transformed with a plasmid-borne repressor protein binding sequence 16, i.e., an operator, and a host chromosomal copy of a gene encoding a repressor protein 12. Another chromosomal gene 14, the product of which is essential for growth or survival of the host cell, is operatively associated with (i.e., placed under the control of) an operator 16 that binds the repressor protein. In the absence of plasmid 15, binding of repressor to the chromosomal operator prevents expression of the essential gene, and the cell can only grow in the presence of inducer. Subsequent introduction of a plasmid that contains a binding site for the repressor protein results in the titration of the repressor protein away from the chromosomal operator, thus allowing expression of the essential gene. Therefore, in the absence of inducer, only those cells that contain the plasmid will grow. This is because the presence of the operator sequence on the plasmid allows the plasmid to titrate the repressor, thus removing repressor molecules which would otherwise be available for binding to the chromosomal operator. Titration of repressor by plasmid operator sequences allows for expression of the essential chromosomal gene, and growth of only those cells containing plasmid. If the host strain is engineered so that repressor is synthesized at a high copy number, then the plasmid will be maintained at an even higher copy number.

As shown in FIG. 2, the plasmid 15 need only include sequences for operator binding 16, and origin of replication 18, and a cloning site 20.

Repressor/Operator Systems Useful According to the Invention

The invention can be used with any trans-acting repressor/operator system. For example, the novel repressor titration system described herein may include any repressor that has a sufficient affinity for its DNA binding sequence such that it is capable of preventing expression of an essential chromosomal gene, but is also titratable by a plasmid-borne DNA binding sequence.

The essential chromosomal gene which is susceptible to repression by the repressor is rendered susceptible to repression in that it is placed under the control of an operator/promoter that binds the repressor, or the repressor binding sequence (i.e., operator) is inserted into the natural promoter of the essential gene in such a way that it can prevent transcription when bound by repressor, but does not disrupt the ability of the natural promoter to initiate transcription of the essential gene in the absence of repressor binding.

More than one different essential gene may be present in the chromosome, e.g., two or three genes, each gene being functionally linked to an operator sequence and thus susceptible to repression by the repressor. The presence of different repressor-susceptible essential genes on the chromosome, preferably at different positions in the chromosome, reduces the possibility of loss of plasmid stability via a mutation or deletion resulting in loss of repression of an essential chromosomal gene.

The repressor is encoded by a chromosomal gene. According to the invention, one or more, preferably one, two, or three, copies of the chromosomal repressor gene are present in the host cell. The chromosomal repressor gene may be a naturally occurring gene which has not been modified, or it may contain a genetic mutation that renders the repressor molecule of higher or lower affinity with respect to the strength of binding to its corresponding operator. Such mutations are known in the prior art. Alternatively, the sequences which initiate expression of the repressor gene may be mutated or genetically engineered such that a higher or lower number of repressor molecules are made in the cell. The number of repressor molecules present in the cell will be related to the copy number of the plasmid bearing the corresponding operator sequence. According to the repressor titration system of the invention, the concentration of repressor present in the host cell is such that, in the absence of the plasmid, the essential gene of interest is not expressed, but in the presence of the plasmid, repressor is titrated away from the essential gene. Where more than one copy of the repressor gene is present in the chromosome, e.g., two or three copies, the amount of repressor protein made in the cell will be increased relative to the presence of one gene; this increase will be taken into account when selecting a corresponding plasmid origin of replication, and in selecting the number of chromosomal operator/essential genes which are present in the cell.

Repressor systems useful according to the invention include but are not limited to the following. The E. coli lac repressor is described in "The Lactose Operon", J. Beckwith, in *Escherichia coli and Salmonella typhimurium*, Eds., J. L. Ingraham et al., 1987 Amer. Soc. Micro., pp. 1444–1452, and Dickson et al., 1975, Science 187;27–35. The lac operon is regulated as follows. Under non-inducing conditions (such as growth on glucose) LacI binds to the operator of the lac operon and prevents transcription of LacZ (β-galactosidase), LacY (lactose permease) and LacA (a transacetylase). Under inducing conditions (such as growth on lactose or addition of IPTG, a non-metabolizable analog) the repressor no longer binds to the operator and transcription occurs. The expression of the operon is easily detected by assay for β-galactosidase.

The above-described plasmid maintenance method is broadly applicable to any host cell susceptible to transfection, such as bacteria (both gram-positive and gram-negative), cultured- or explanted vertebrate cells (e.g., mammalian stem cells) and yeast.

The Lac repressor, while it will not itself function as a transcriptional regulator in eukaryotic systems, is of use in the invention for the maintenance of plasmids in yeast. Its DNA binding capacity can be used to modulate the activity of a yeast transcriptional activator in the manner described below (see also Example 5).

A consensus Lac repressor binding site (operator) is defined as the following DNA sequence:

5'-GGAATTGTGAGCGGATAACAATT-3' [SEQ ID NO: 2]

The Lac repressor will bind to this site with high affinity, $k_D$ in the range of $1 \times 10^{-14}$ M. This affinity is considerably higher than that of most yeast transcriptional activator proteins; therefore it is envisaged that a promoter in which a Lac repressor binding site is coincident with the binding site for a yeast transcriptional activator protein will be used to modulate the DNA-binding activity, and hence the function, of the yeast protein. For example, the well-characterized yeast activator protein Gal4p has a consensus binding site of $CGGN_5(A/T)N_5CCG$ [SEQ ID NO: 1]—where N can be any nucleotide (Liang et. al., 1996, *Mol. Cell. Biol.*, 16: 3773–3780). Thus the hybrid sequence below based around the Lac operator, with the Gal4p consensus site shown in bold typeface, will be competent in binding both the Lac repressor and Gal4p:

5'-GGAATTGTGAGCGGATAACAATTTCCCG-3' [SEQ ID NO: 3]

The affinity of Gal4p for its consensus DNA binding site is lower than that of the Lac repressor for its site ($k_D$ approximately $1 \times 10^{-9}$ M). The crystal structure of the DNA binding domain of Gal4p bound to its site (Marmorstein et. al., 1992, *Nature*, 356: 408–414) stresses the importance of the CGG triplets at either end of the DNA binding site as the regions of the site that are directly contacted by the protein. Given that one of the CGG triplets is in the center of the Lac repressor binding site, a region in which mutations dramatically reduce the affinity of LacI binding and makes direct contacts with the protein (Lewis et. al., 1996, *Science*, 271: 1247–1254). Therefore, it is anticipated that LacI and Gal4p will not be able to occupy the hybrid site simultaneously.

One of skill in the art will appreciate that certain modifications may be made to the repressor-titration system described herein which serve to adapt the system to a given protocol. For example, similar operator sequences to the consensus Lac operator [SEQ ID NO: 2] can be used in order to obtain hybrid sequences useful in the present invention. Similar operator sequences are disclosed in Oehler et al., 1990, *EMBO J.*, 9(4): 673–679 and Müller, 1996, *J. Mol. Biol.*, 257: 21–29. Furthermore, where the growth medium contains components which induce rather than allow for repression of the operator, and inducing conditions are not desired during growth, operator or repressor mutants may be used to overcome induction and allow for repression. One example of a mutant repressor is a LacI mutant of the lac repressor. A LacI mutant no longer has the capacity to bind inducer. Examples of LacI mutants include, e.g., LacI$^s$ mutants (Beyreuthe, 1978, Cold Spring Harbor Laboratory, CSH, N.Y.) and other mutants such as Asp$^{274}$→Asn$^{274}$ (Chang et al., 1994, *Biochem.*, 22: 3607–3616). By replacing the wild type repressor with a mutant repressor which is insensitive to inducer, the repressor is able to bind to the operator during growth, and the plasmid is maintained in the host cell even under conditions which normally induce the lac operon.

The *E. coli* trp repressor also is useful according to the invention (see "The tryptophan Operon", Yanofsky and Crawford, in *Escherichia coli and Salmonella typhimurium*, Eds., J. L. Ingraham et al., 1987, Amer. Soc. Micro., pp. 1453–1472). The trp repressor is present at about 50 copies/cell, and requires the presence of tryptophan in the fermentation medium as an inducer of repressor binding. The *E. coli* galR repressor also is useful according to the invention (see "The Galactose Operon", S. Adhya, in *Escherichia coli and Salmonella typhimurium*, Eds., J. L. Ingraham et al., 1987, Am. Soc. Micro., pp. 1503–1512). The *E. coli* araC repressor is also useful according to the invention (see "The L-Arabinose Operon", R. Schlief, In *Escherichia coli and Salmonella typhimurium*, Eds., J. L. Ingraham et al., 1987, Am. Soc. Micro., pp. 1473–1481; Dunn et al., 1984, *Proc. Natl. Acad. Sci. U.S.A.*, 81: 5017–5020). The araC repressor has increased binding affinity in the presence of arabinose. Finally, the λ repressor is useful according to the invention (Introduction to Lambda Phages, in *Current Protocols in Molecular Biology*, Eds. Ausubel, et al., 1994, Section III, Unit 1.9; Hochschild et al., 1986, *Cell*, 47(5): 807–816).

Host Cells Useful According to the Invention

Organisms are currently being developed as vectors for the delivery of therapeutic or prophylatic agents including DNA, RNA, proteins, non-proteinaceous compounds, and viruses. Such vector microorganisms include bacteria such as Clostridium (Parker et al., 1947, *Proc. Soc. Exp. Biol. Med.*, 66: 461–465; Fox et al., 1996, *Gene Therapy*, 3: 173–178; Minton et al., 1995, *FEMS Microbiol. Rev.*, 17: 357–364), Salmonella (Pawelek et al., 1997, *Cancer Res.*, 57: 4537–4544; Saltzman et al., 1996, *Cancer Biother. Radiopharm.*, 11: 145–153; Carrier et al., 1992, *J. Immunol.*, 148: 1176–1181; Su et al., 1992, *Microbiol. Pathol.*, 13: 465–476; Chabalgoity et al., 1996, *Infect. Immunol.*, 65: 2402–2412), listeria (Schafer et al., 1992, *J. Immunol.*, 149: 53–59; Pan et al., 1995, *Nature Med.*, 1: 471–477) and Shigella (Sizemore et al., 1995, *Science*, 270: 299–302), as well as yeast, mycobacteria, slime molds (members of the taxa Dictyosteliida—such as of the genera Polysphondylium and Dictystelium, e.g. *Dictyostelium discoideum*—and Myxomycetes—e.g. of the genera Physarum and Didymium) and members of the Domain Arachaea (including, but not limited to, archaebacteria), which have begun to be used in recombinant nucleic acid work, members of the phylum Protista, or other cell of the algae, fungi, or any cell of the animal or plant kingdoms.

Mammalian cells are of use in the invention, particularly for ex vivo gene therapy. Such cells include, but are not limited to, cells of the immune system (such as T-cells, B-cells and macrophages), fibroblasts, hematopoietic cells and dendritic cells. Using established technologies, stem cells (e.g. hematopoietic stem cells) may be used for gene transfer after enrichment procedures. Alternatively, unseparated hematopoietic cells and stem cell populations may be made susceptible to DNA uptake.

As discussed above, numerous host microorganisms are of use in the invention. Among these are numerous gram positive and negative bacteria (see above), as well as yeast strains in which a plasmid exists that is capable of being maintained at medium—to high copy number, which will be considered in somewhat more detail below.

a. Bacteria

Gram negative bacteria useful according to the invention include but are not limited to *E. coli*, Shigella and Salmonella, e.g., *S. typhimurium*.

Gram positive species useful according to the invention include but are not limited to Bacillus and Lactococcus, for which high copy number plasmids already exist, as well as Clostridium and Listeria. Examples of plasmids useful according to the invention in Lactococcus are pNZ2123 and pIL253 (Simon et al., 1988, *Biochimie*, 70: 559). The lactococcal lactose operon has been used to control the expression of heterologous proteins (Wells et al., 1993, *Mol. Microbiol.*, 8(6): 1155–1162). This operon utilizes the lacR repressor (van Rooigen et al., 1990, *J. Biol. Chem.*, 265: 18499–18503) to control the expression of T7 polymerase, which then controls the expression of the heterologous protein.

In Bacillus, e.g., *B. subtilis*, the λ repressor has been used to control the expression of heterologous proteins. The λ repressor has been placed under the control of the sak42D promoter, which can be efficiently transcribed in *B. subtilis* (Breitling et al., 1990, *Gene*, 93(1): 35–40).

Genetically engineered Salmonella have many of the desirable properties of a nucleic acid delivery vector, including tissue-targeting a distant inoculation site, selective replication within the target tissue and the ability to express transgenes, as has been demonstrated for the herpes simplex virus thymidine kinase (HSV TK) in tumors in mice (Pawalek et al., 1997, *Cancer Res.*, 57: 4537–4544, the contents of which are herein incorporated by reference). When wild-type Salmonella were introduced into melanoma-bearing mice, the bacteria were found within the tumor at levels exceeding $10^9$ per gram of tumor tissue. As pathogens, they caused the death of the mice; however, when attenuated strains (in this case hyperinvasive auxotrophic mutants) were used, the tumor-targeting and amplification phenomena were retained, whereas their pathogenicity was limited. (Note that the term "hyperinvasive" refers to a phenotype in which bacterial cells enter cells of another organism, rather than merely occupy intercellular spaces in a tissue.) Tissue targeting was observed to be specific. While the numbers of Salmonella found in tumor cells and in the liver were comparable 5 hours post-inoculation, the tumor:liver ratio ranged between 250:1 and 9000:1 after 2 days. When these auxotrophs were inoculated intraperitoneally into C57B6 mice bearing B16F10 melanomas, they suppressed tumor growth and prolonged average survival to as much as twice that of untreated mice. A plasmid containing the HSV TK gene with a β-lactamase secretion signal was constructed that, when expressed, resulted in translocation to the periplasm and phosphorylation of the prodrug ganciclovir. The results demonstrated that attenuated Salmonella would be useful both for inherent antitumor activity and delivery of therapeutic proteins to tumor cells in vivo.

Salmonella offer several potential advantages as nucleic acid delivery vectors. They can grow under either aerobic or anaerobic conditions such as those that occur within solid tumors (Jain et al., 1994, *Sci. Am.*, 271: 58–65; Lee and Falkow, 1990, *Proc. Natl. Sci. U.S.A.*, 47?: 4303–4308; Ernst et al., 1990, *Infect. Immun.*, 58: 2014–2016; Lee and Falkow, 1994, *Methods Enzymol.*, 236: 531–545; Bajaj et al., 1996, *Mol. Microbiol.*, 22: 703–714); they express specialized systems for invasion into and survival within both epithelial cells and macrophages (Blishka et al., 1993, *Cell*, 73: 903–920; Behlau and Miller, 1993, *J. Bacteriol.*, 175: 4475–4484; Tuomanen, 1993, *Am. Soc. Microbiol. News*, 59: 292–296; Bermudes and Joiner, 1993, *Parasitol. Today*, 9: 458–463; Ginocchio et al., 1994, *Cell*, 76: 717–724; Barinaga, 1996, *Science*, 272: 1261–1263); and there is a vast body of knowledge and powerful genetics in the Enterobacteriaceae. Further, Salmonella repressor-titration host cell lines may be constructed using the methods and plasmids applicable in the construction of comparably useful lines of *E. coli*, which methods and materials are well known in the art, including transduction via phage vectors that include, but are not limited to, P22 phage (see Bachmann, 1977, in *E. coli and Salmonella typhimurium*, *Cellular and Molecular Biology.*, ed. Niedhardt et al., Am. Soc. Microbiol.; Sanderson and Hurley, 1977, ibid.).

To avoid confusion, it should be noted that while the method of the present invention eliminates the need for auxotrophic selection markers to enable retention of the minimal plasmid, auxotrophic host strains of Salmonella are typically used both to attenuate virulence and to target necrotic or apoptotic tissues (which environments provide needed nutrients not provided by normal tissues), such as are found within solid tumors, ulcers or tissues that are targets for autoimmune destruction or other pathological wasting; host cell auxotrophy is independent of the mechanism of stable plasmid maintenance. Auxotrohpic mutations that are of use in the invention include, but are not limited to, those affecting the biosynthesis of purines (Bacon et al., 1951, *Br. J. Exp. Pathol.*, 32: 85–96) or aromatic amino acids (Hoiseth and Stocker, 1981, *Nature*, 291: 238–239), or combinations of such mutations (O'Callaghan et al., 1988, *Infect. Immunol.*, 56: 419–423). Auxotrophic lines of Salmonella and may be constructed and tested for tissue invasiveness and specificity of targeting, safety to the patient, dosage and therapeutic efficacy (when tranformed with the stably-maintained plasmid of the present invention) in the mouse model, all as described by Pawalek et al. (1997, supra). These methods are summarized briefly below.

Bacteria useful for the construction of auxotrophic lines include wild-type *Salmonella typhimurium* strains, as well as other strains (which may, themselves, be auxotrophic if polyauxotrophs are desired); several attenuated (or "vaccine") *S. typhimurium* strains are described by Nakayama et al., 1988, infra. Of particular use is wild-type strain 14028 (ATCC CDC6516-60). Alternatively, auxotrophic cell lines may be obtained from the American Type Culture Collection. The procedure for generating auxotrophs from wild-type cells is briefly summarized as follows:

Cells of strain ATCC 14028 or another strain are mutagenized with 50 $\mu$g/ml nitrosoguanidine (20 min at 37° C.) and UV irradiation (50 J/m$^2$, λ=254 nm; see Miller, 1992, *A Short Course in Bacterial Genetics*, Cold Spring Harbor Laboratory Press, Cold Spring Harbor, N.Y., pp. 143–156). Virulence of the resulting auxotrophs is tested by injecting groups of tumor-bearing mice (e.g. of strain C57B6) intraperitoneally with $10^6$ bacteria and measuring the mean time to death (Bacon et al., 1951, supra). This method, in contrast witht the LD$_{50}$ method, is said to yield reproducible, statistically significant results with fewer mice. The mice are allowed to eat and drink ad libitum, and the cages are monitored for dead or moribund mice. All surviving animals are euthanized 10, 30, or 60 days after inoculation with bacteria, as desired. Data are expressed as mean±SD (standard deviation) survival after inoculation with bacteria (in days); in order to be deemed safe for administration to a recipient organism according to the methods of the invention, the rate of survival of test animals at a given cell dosage must be no more than 10%, ideally 1–5% lower than that of control animals receiving only a cell-free carrier, rather than the auxotrophic cells, following tumor formation; preferably, the rate of survival of Salmonella-treated animals will be equal to- or even greater than that of control animals.

It has been found that inoculi of 1–4×$10^5$ cfu/mouse of the polyauxotrophs administered intraperitoneally (Pawalek et al., 1997, supra) are not lethal for at least 28 days, and some strains of mice tolerate inoculi as high as 5×$10^7$ cfu; doses in the range of $10^5$ cfu are said to be the most useful for investigating the several different factors that need to be taken into account (virulence, tumor targeting, amplifcation and growth suppression). Eight days following tumor implantation, mice are further inoculated intraperitoneally with $4 \times 10^6$ cfu of the candidate auxotrophic cells. Ten days following inoculation of bacteria, mice are given Baytril (enrofloxacin 0.2 mg/ml in drinking water) for a total of 2 weeks, a treatment that is said to result in a moderate increase in survival of mice. Tumor growth is assessed by periodic caliper measurements (in mm). Tumor volume is computed by the formula: length×width×height×0.5236=volume (in mm$^3$). Animals are euthanized when their tumors reach 4000 mm$^3$ or when they become moribund.

Testing of auxotrophs for tissue invasiveness and targeting first may be performed in vitro in cultured animal cells (e.g. human melanoma cells), for example in Corning tissue culture flasks (25 cm$^2$) with the use of gentamicin sulfate, as modified from Lee and Falkow (1994, supra). Following 15- or 30-min invasion periods and 30-min incubations with 50 µg/ml gentamicin, animal cells are quantitated in a Coulter counter (Coulter Electronics, Inc.), and bacteria are quantitated by serial dilutions on LB agar; data are expressed as the number of infecting (gentamicin-resistant) bacteria/$10^6$ animal cells.

If so desired, auxotrophic cells additionally may be tested in a mouse tumor model, also as described (Pawalek et al., 1997, supra); note that the techniques employed are equally applicable to use in an animal system which models other necrotic or apoptotic cell populations. In brief, mice (e.g. C57B6 or DBA/2J mice) are inoculated subcutaneously in the shoulder region with $5 \times 10^5$ B16F10 and Cloudman 591 mouse melonoma cells, respectively. Alternatively, BALBc nu/nu mice may be inoculated with $2 \times 10^7$ cells of human lung carcinoma A549, human colon carcinoma HCT 116, human breast carcinoma BT20, human renal carcinoma CRL 1611, or human hepatoma HTB 52. When palpable tumors develop, mice are further inoculated intraperitoneally with cells of the Salmonella auxotrophic line being tested ($10^2$ to $10^8$, preferably about $10^6$ colony-forming units). At time points 5 hours, 2 days and 4 days after inoculation, the animals are sacrificed, and the tumors and livers are removed and weighed. A central portion of a tumor from each animal is prepared for microscopy, and the remainder of the tumor is homogenized in 5 volumes of LB broth (see Sambrook et al., 1989, *Molecular Cloning, A Laboratory Manual 2nd Edition*, Cold Spring Harbor Laboratory Press, Cold Spring Harbor, N.Y.) per gram of wet weight tissue and quantitated for bacteria by serial dilution on LB agar plates. After incubation of the plates for a time sufficient to allow growth of visible bacterial colonies, the plates are scored for the numbers of colonies resulting from infiltration and survival of bacterial cells in each tumor.

For light microscopic analyses, portions of the tumor are fixed in formalin, embedded (e.g. in paraffin), sectioned and stained with H&E (hematoxylin/eosin) or tissue Gram's stain (Brown-Brenn stain). For EM, the tissue is fixed in half-strength Karnovsky's fixative for 6 hours at 4° C., followed by washing in cacodylate buffer overnight, post-fixation with 1% OsO$_4$ and 1.5% potassium ferrocyanide in cacodylate buffer for 2 hours and embedding in Spurr's resin. Ultrathin sections (less than 6 µm thickness) are stained with uranyl acetate and lead citrate and photographed through an electron microscope (e.g., a Zeiss 109 EM).

Prior to the mutation of an essential gene and introduction of an operator-linked copy of it to the potential Salmonella host cells for the maintenance of plasmids of the invention, it is necessary to determine the stability of the auxtrophic phenotype of the cell line in a recipient individual. To do this, the mouse tumor model is again used. Tumors are excised from mice at least two, and preferably five or more, days after administration of the Salmonella auxotrophs; the excised tissue is then homogenized (for example, using a blender or Dounce homogenizer, sonicator or freeze/thaw cycle). Bacteria from the resultant tumor homogenates are replicate-plated onto minimal medium agar supplemented with the appropriate nutritional addives to monitor for the presence of the auxotrophic mutations. Minimum values (expressed as colony-forming units per gram of tumor tissue) of at least $10^3$, preferably up to $10^6$, and more preferably in the range of $10^{7-10^{10}}$ are indicative of stablility of the auxotrophic phenotype. Phenotypically stable lines may then be engineered for use as plasmid hosts in the repressor titration system of the present invention.

The nucleic acid vector to be transfected into the Salmonella host cells for stable maintenance according to the invention is constructed by the methods and using sequences described herein above and below. Methods by which Salmonella host cells may be transformed include, but are not limited to, electroporation (O'Callaghan and Charbit, 1990, *Mol. Gen. Genet.*, 223: 156–158, the contents of which are herein incoporated by reference) and other transformation methods known in the art (see Hanahan et al., 1991, *Methods Enzymol.*, 204: 63–113).

Expression in Salmonella of the product of the therapeutic- or other gene present on the stably-maintained plasmid may be assayed by biochemical methods including, but not limited to, enzymatic assay and immunological detection. For example, thymidine kinase activity may be assayed using the protocol of Summers and Summers (1977, *J. Virol.*, 24: 314–318) as modified by Pawalek et al. (1997, supra), containing 0.2 mM I-dC, 0.01 mM $^{125}$I-dC, 10 mM ATP, 0.6 mg/ml BSA, 10 mM MgCl$_2$, 25 mM NaF, and 100 mM sodium phosphate buffer, pH 6.0. Five ml of a protein sample from transformed Salmonella is combined with 20 ml of the reaction mix, incubated at 37° C. for 1 h, bound to DE81 paper (Whatman) and washed. The associated radioactivity is quantified in a gamma counter, such as a liquid scintillation counter.

Alternatively, SDS-PAGE may be performed on bacterial lysates according to Weber and Osborn (1975, in: H. Neurath and R. Hill, eds., *The Proteins*, Ed. 3, Vol. I, Academic Press, New York, pp. 179–223, herein incorporated by reference) or immunoblots are performed according to Towbin et al (1979, *Proc. Natl. Acad. Sci, U.S.A.*, 76: 4350–4354). Primary anti-antibodies to many antigens may be obtained from commercial or other public sources (e.g. ATCC), or may be prepared by methods well known in the art. Secondary antibodies prepared against immunoglobulins of numerous species (including, but not limited to, rat, mouse, rabbit and goat) and suitable for use in a number of chromogenic, chemiluminescent and fluorescent detection protocols are commercially available (for example, from Promega, Madison, Wis.; Vector Laboratories, Burlingame, Calif.). Antibody dilution, incubations and detections are performed according to manufacturer's suggested conditions.

If a therapeutic or other gene of interest on the stably-maintained plasmid is functionally linked to a secretion signal (e.g. the β-lactamase signal whose use is described by Pawalek et al., 1997, supra), translocation of the protein to the periplasmic space may be assayed by performing either of the above detection procedures on periplasmic protein extracts. Periplasmic fractions are collected using a modified osmotic shock procedure (Randall and Hardy, 1986, *Cell*, 46: 921–928; Klein et al., 1992, *Protein Eng.*, 5: 511–517, both incorporated herein by reference). Cultures are grown overnight at 37° C. with shaking in medium consisting of LB with either 100 μg/ml ampicillin or 10 μg/ml tetracycline. One ml of bacteria culture is pelleted and resuspended in 100 μl of Tris-acetate (0.1 M). Eight ml of lysozyme (2 mg/ml) are added and the mixture is kept at room temperature for 10 minutes. 100 μl of ice-cold $H_2O$ containing 1 mM phenyl-methylsulfonyl fluoride (PMSF) is added and the mixture is further incubated on ice for 5 minutes. Four μl of $MgSO_4$ (1 M) are added to stablize the spheroplasts, which are then pelleted in a micofuge for 40 seconds at 12,000×g. The spheroplast pellet and the supernatant periplasmic fraction may be compared with the whole unfractionated bacteria either by gel electrophoresis and immunoblotting.

In the specific example provided by Pawalek et al., the therapeutic gene borne by the transformed Salmonella was herpes simplex virus thymidine kinase. One may assay the effect of this gene on mouse tumors, as might be done is this gene were incorporated onto a stably-maintained plasmid of the present invention, as follows: Eight days post-tumor implantation, mice are divided into test and control groups. Test mice are further inoculated intraperitoneally with $10^5$ cfu of auxotrophic Salmonella bearing the HSV TK gene-containing plasmid of the invention, which gene is preferably operatively-linked to a β-lactamase secretory signal sequence. At 11 days post-tumor implantation, GCV (GCV sodium, Cytovene; Syntex Laboratories, Palo Alto, Calif.) is inoculated intraperitoneally into groups of mice under the following protocols: (a) 330 mg/kg (2.5 mg, day 11; 2.5 mg, day 12; 2.5 mg, day 18; and 1.25 mg, day 19); (b) 220 mg/kg (2.5 mg, day 11; 2.5 mg, day 12); (c) 165 mg/kg (2.5 mg, day 11; 1.25 mg, day 12); (d) 110 mg/kg (1.25 mg, day 11; 1.25 mg, day 12); (e) 55 mg/kg (1.25 mg, day 11); (f) 0 mg/kg. At 18 days post-tumor implantation (10 days post-bacterial inoculation), all animals are given enrofloxacin (Baydril, 0.2 mg/ml) in their drinking water, and they are maintained on this antibiotic for 2 weeks. Tumor growth is then measured in all animals, as described above, and compared among groups. Efficacy of treatment according to this model is judged to be a reduction in the rate of tumor size increase of at least 2- to 10-fold, preferably 20- to 100-fold and even up to 200- to 1000-fold. Regression of at least 5% of tumor burden in treated animals relative to untreated controls is indicative of effective treatment according to the invention; preferably, such a loss of tumor cell mass is up to 10%, more preferably up to 50%, and most preferably up to 75% or even 100% of the total present.

b. Yeast

Yeasts are useful according to the invention, as described below. The advantages of using repressor titration for yeast plasmid maintenance include:

1. Plasmid size. Yeast plasmids tend to be large. Most plasmids bearing the 2μ circle are between 5 and 8 kb in length. For example, YEp24 is 7. kb, and the YEplac series of plasmids (Gietz and Sugino, 1988, *Gene*, 74: 527–534) vary between 5 and 6 kb. The 2μ sequence itself is approximately 1.5 kb in length. The remaining plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses and the sizes quoted encompassing the coding sequence, together with the promoter and terminator elements required for correct expression):

TRP1 (Phosphoribosylanthranilate isomerase, which is a component of the tryptophan biosynthetic pathway). Approximately 1 kb in length.

URA3 (Orotidine-5'-phosphate decarboxylase, which takes part in the uracil biosynthetic pathway). Approximately 1.2 kb in length.

LEU2 (3-Isopropylmalate dehydrogenase, which is involved with the leucine biosynthetic pathway). Approximately 1.7 kb in length.

HIS3 (Imidazoleglycerolphosphate dehydratase, or IGP dehydratase). Approximately 2.4 kb in length.

LYS2 (α-aminoadipate-semialdehyde dehydrogenase, part of the lysine biosynthetic pathway). Approximately 4.6 kb in length.

A significant advantage of the repressor titration system is that the same minimal plasmid may be propagated in both bacteria and yeast without the use of different marker and maintenance systems. In addition, use of the repressor titration system employing a single repressor binding site recognized in both bacterial and yeast repressor-titration host strains reduces plasmid size to approximately 2.5 kb or less.

2. Plasmid copy number. The system is more manipulative, with many repressors, repressor copy numbers and repressor binding affinities being available. This flexibility can be manipulated to increase yeast plasmid copy number, e.g. for increased recombinant protein production.

3. Metabolic burden. Expression of multiple plasmid borne copies of selectable markers can represent a greater metabolic burden to the host than expression from a single chromosomal copy.

4. Yeast auxotrophic markers require the use of expensive defined media. Complex rich media cannot be used without losing selection pressure. The biomass concentrations achievable from yeast cultures could be increased using repressible non-metabolic (e.g. structural, DNA synthesis etc.) essential yeast genes without the use of antibiotics.

5. Production of plasmids and yeast artificial chromosomes which do not carry selectable marker genes for gene therapy.

6. Tight transcriptional control to aid the study of yeast gene function. The majority of yeast expression systems permit low-level transcription of genes which are are intended to be repressed or activated specifically in order that the effect of the loss of their product can be assessed. Prior art methods for the study of many yeast genes entail their fusion to constitutive promoters (e.g., ADH1) for positive regulation, while the GAL1 (galactose) or CUP1 (copper) promoters, which both display leaky expression patterns (particularly CUP1, which may be induced by trace amounts of copper present in water or the cell growth medium), are regularly used when inducible expression is required. The repressor titration system of the present invention may be of use in achieving tight transcriptional control of such genes.

A yeast repressor-titration host cell strain may be constructed as follows:

JPY5::Δ80 (genotype: MATα, ura3-52, his3Δ200, leu2Δ1, trp1Δ63, lys2Δ385, gal80::TRP1) is an example of a yeast strain that is of use in the construction of host cell lines according to the invention. This strain has deficiencies in uracil, histidine, leucine and lysine biosynthesis. The GAL80 gene has been deleted using the TRP1 gene. This is important, in that it allows constitutive Gal4p-mediated transcriptional activation. Three steps are required in order to render JPY5::Δ80 a functional repressor-titration host strain:

1. Inactivation of the Endogenous Essential Gene.

Figure 3:
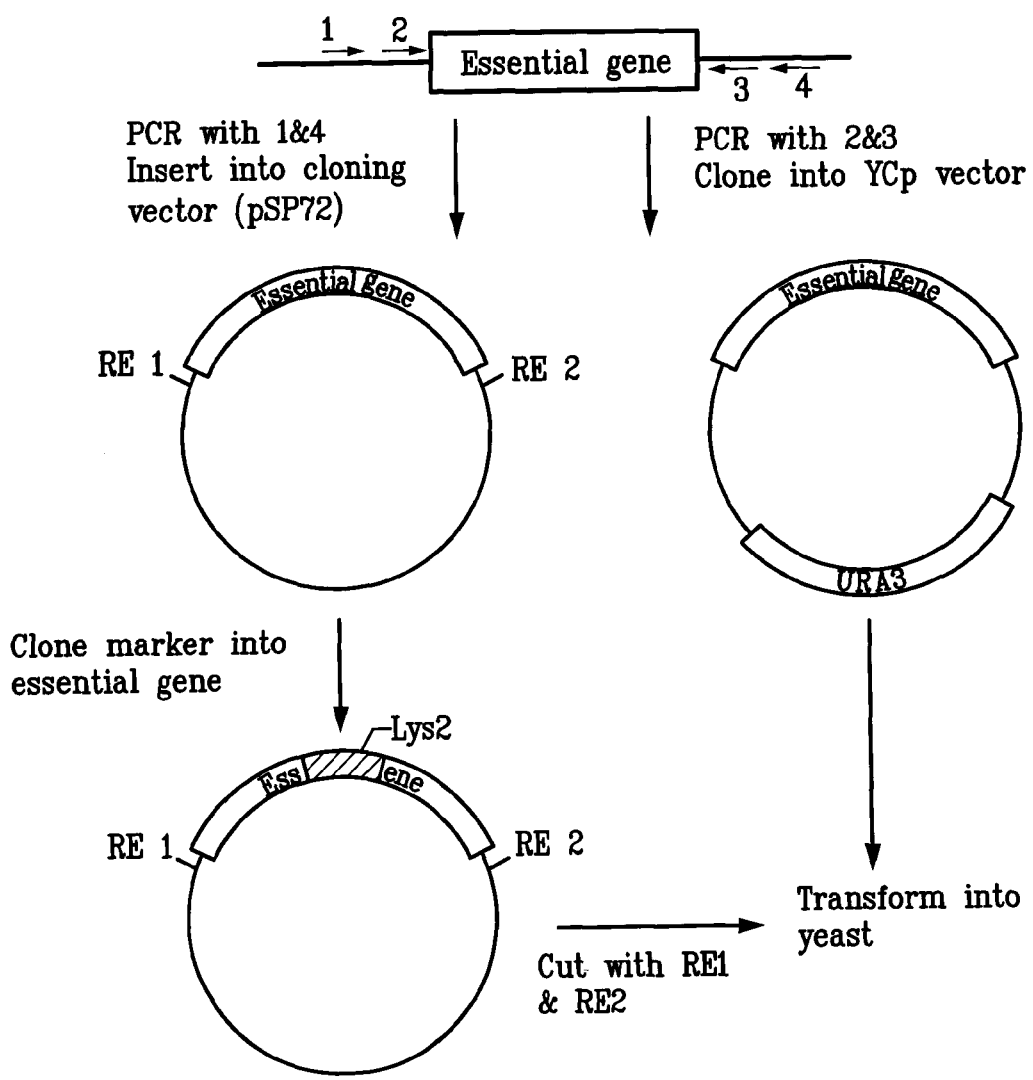
FIG. 3 is a schematic drawing of the construction of a yeast repressor-titration host cell strain.

The general scheme (adapted from Boeke et al., 1987, *Methods Enzymol.*, 154: 164–175, herein fully incoporated by reference) is shown in FIG. 3. The essential gene is cloned into two vectors. The first, a general cloning vector such as pSP72, is used to make a disrupted version of the essential gene; in the case shown, LYS2 is inserted into the essential gene to knock out its function. This plasmid is propagated only in bacteria. The LYS2 gene surrounded by the remainder of the essential gene is excised from the plasmid using restriction enzymes (RE1 and RE2, as indicated). The second vector to be constructed bears the essential gene (driven from its own promoter) on a yeast replicating vector bearing the URA3 gene. Yeast cells are co-transformed with this yeast vector and with the linearized DNA fragment bearing the LYS2 gene surrounded by the remainder of the essential gene. Selection for transformants is made on media lacking uracil and lysine. The DNA fragment integrates into the endogenous copies of the essential gene by homologous recombination to ablate their function, and the essential gene phenotype is then maintained by the exogneous (plasmid-borne), operator-linked copy of that gene.

2. Construction of lacI/Gal4p Operator to Control Essential Gene Expression.

The lacI/Gal4p composite operator is constructed (see below) into a plasmid bearing a LEU2 marker. This is placed upstream (5') of a minimal promoter reporter construct (e.g., CYC1/lacZ or GAL1/lacZ) to ensure that Gal4p will activate gene expression under appropriate conditions. The reporter gene is then replaced with the essential gene by molecular methods well known in the art, and the resulting plasmid introduced into the yeast cells generated in step 1 via plasmid shuffling, as described by Boeke et al., 1987, supra. Transformants are grown on 5-FOA to select against the plasmid-borne wild-type copy of the essential gene, and on media lacking leucine to select for the essential gene which is regulated by the lacI/Gal4p composite operator, thereby replacing the wild-type essential gene with its operator-linked counterpart. As an alternative procedure, it is contemplated that the composite expression vector may be introduced into the repressor-titration host cell at the same time that the wild-type plasmid copy is deleted.

3. Expression of lacI in Yeast Cells.

The lacI coding seuqence is cloned upstream of the ACT1 promoter in an integrating plasmid bearing the HIS3 marker. The resulting construct is cut in the HIS3 gene and integrated at the HIS3 loci (one on either chromosome) of the yeast cells resulting from the steps above. This strain will grow only in the presence of a plasmid bearing a lacI binding site which titrates the repressor from the ACT1 promoter, permitting HIS3 transcription.

Plasmids Useful According to the Invention

The invention can be utilized advantageously with a plasmid origin of replication that permits replication of at least 10, preferably at least 20–100, and most preferably at least 200–500 copies of the plasmid per host cell. Those origins of replication that permit replication of moderate (i.e., 20–50) to high plasmid (i.e., 200–500) copy numbers are especially useful in that moderate to high plasmid copy numbers can easily titrate repressor molecules. Of course, if desired, a plasmid having a copy number as high as 1000–2000 copies per cell also may be used. Plasmids with low copy numbers (i.e., 10 copies or less) are most advantageously used according to the invention after mutation to bring about increased copy number (J. Scott, 1984, Microbial Reviews 48:1–23).

a. Bacterial Plasmids

Of the frequently used origins of replication, pBR322 (20 copies/cell) is useful according to the invention, and pUC (at 200 copies/cell) is preferred. Although not preferred, other plasmids which are useful according to the invention are those which require the presence of plasmid encoded proteins for replication, for example, the pT181, FII, and FI origins of replication.

Examples of origins of replication which are useful according to the invention in *E. coli* and *S. typhimurium* include but are not limited to, pHETK (Garapin et al., 1981, *Proc. Natl. Acad. Sci. U.S.A.*, 78: 815–819), p279 (Talmadge et al., 1980, *Proc. Natl. Acad. Sci. U.S.A.*, 77: 3369–3373), p5-3 and p21A-2 (both from Pawalek et al., 1997, supra), pMB1 (25 or more copies per cell, Bolivar et al., 1977, *Gene*, 2: 95–113), ColE1 (15 or more copies per cell, Kahn et al., 1979, *Methods Enzymol.*, 68: 268–280), p15A (about 15 copies per cell, Chang et al., 1978, *J. Bacteriol.*, 134: 1141–1156); pSC101 (about 6 copies per cell, Stoker et al., 1982, *Gene*, 18: 335–341); R6K (less than 15 copies per cell, Kahn et al., 1979, supra); R1 (temperature dependent origin of replication, Uhlin et al., 1983, *Gene*, 22: 255–265); lambda dv (Jackson et al., 1972, *Proc. Natl. Acad. Sci, U.S.A.*, 69: 2904–2909); pYA (Nakayama et al., 1988, infra). An example of an origin of replication that is useful in Staphylococcus is pT181 (about 20 copies per cell, J. Scott, 1984, *Microbial Reviews* 48: 1–23). Of the above-described origins of replication, pMB1, p15A and ColE1 are preferred because these origins do not require plasmid-encoded proteins for replication.

b. Yeast Plasmids

Three systems are used for the recombinant plasmid expression and replication in yeasts:

1. Integrating. An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, *Methods in Yeast Genetic*, Cold Spring Harbor Laboratory Press, Cold Spring Harbor, N.Y.). The cells are treated with lithium acetate to achieve transformation efficiencies of approximately $10^4$ colony-forming units (transformed cells)/$\mu$g of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS1), a sequence of approximately 700 bp which, when carried on a plasmid, permits its replication in yeast, and a centromeric sequence (CEN4), the latter of which allows mitotic stability. These are usually present at 1–2 copies per cell. Removal of the CEN sequence yields a YRp plasmid, which is typically present in 100–200 copes per cell; however, this plasmid is both mitotically and meiotically unstable.

3. High-copy-number $2\mu$ circles. These plasmids contain a sequence approximately 1 kb in length, the $2\mu$ sequence, which acts as a yeast replicon giving rise to higher plasmid copy number (approximately 100 copies/cell); however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

Repressor titration plasmid maintenance is relevant to the latter two systems.

As suggested above, examples of yeast plasmids useful in the invention include the YRp plasmids (based on autonomously-replicating sequences, or ARS), which have copy numbers up to about 100 copies per cell, and the YEp plasmids (based on the $2\mu$ circle), with a copy number of 50–100 per cell. (See Sikorski, "Extrachromsomoal cloning vectors of *Saccharomyces cerevisiae*", in *Placmids, A Practical Approach*, Ed. K. G. Hardy, IRL Press, 1993; and *Yeast Cloning Vectors and Genes, Current Protocols in Molecular Biology*, Section II, Unit 13.4, Eds., Ausubel et al., 1994). Yeasts are able to express the *E. coli* lacZ gene, it is therefore contemplated according to the invention to use the lac repressor titration system to control the expression of yeast genes such as ura3 or leu2, which have been used for the maintenance of plasmids in yeasts (Gunge, 1983, *Ann Rev. Micro.*, 37: 253–276) or of essential genes (see below).

Essential Genes Useful According to the Invention

The invention may be used in conjunction with a number of different essential chromosomal host genes for the stable maintenance of the plasmid. These essential genes include but are not limited to the following categories, e.g., genes encoding products related to the biosynthesis of cell metabolites, genes whose products are involved in carbon metabolism, genes coding for antibiotic resistance, and genes encoding the biosynthesis or regulation of macromolecules, e.g., genes essential for DNA and/or RNA synthesis and replication functions.

a. Bacteria

1. Essential Genes Encoding Products Related to Synthesis of Components of Cell Structure.

Certain genes encoding enzymes involved with the supply of cell components, in particular the supply of cell wall precursors, are also essential for host cell growth and are useful according to the invention. For example, the bacterial cell wall contains meso-diamiopimelic acid (DAP), and an inability to synthesize this component results in cell lysis. It has been demonstrated that mutants in which the asd gene (aspartate β-semialdehyde dehydrogenase) or dapD gene (tetrahydrodipicolinate N-succinyltransferase; Baril et al., 1992, *J. Gen. Microbiol.*, 138: 47–53) are deleted can be used for the maintenance of plasmids that carry a complete copy of that gene on the plasmid (Nakayama et al., 1988, *Bio/technology*, 6: 693–697; DeGryse, U.S. Pat. No. 5,198,343). A number of other genes in the DAP biosynthetic pathway could also be used, namely dapA, dapB, dapC and dapE genes. dapA and dapB have been cloned and all dap genes have been sequenced (Blattner et al., 1997, *Science*, 277: 1453–1462), and dapB is available as a single cistron (Richaud et al., J. Bacteriol. 166:297–300, 1986; Bouvier et al., 1984, *J. Biol. Chem.*, 259: 14829–14834). The genes involved in the biosynthesis of other cell wall components, such as D-alanine biosynthesis, are also useful according to the invention (Walsh, 1989, *J Biol. Chem.*, 264(5): 2393–2396). A DNA sequence encoding a component for D-alanine has been used for the stabilization of plasmids without using antibiotics (see EP 85/309020).

The invention contemplates the use of repressor titration in conjunction with such genes. The gene of interest is first deleted from the host strain such that the host now has a requirement for the product of that gene (Winans et al., 1985, *J. Bacteriol.*, 161(3): 1219–1221; Jasin et al., 1984, *J. Bacteriol.*, 159(2): 783–786). A copy of the gene is then constructed using conventional cloning techniques so that its expression is directed by the promoter/operator which binds the chosen repressor protein. This construct is then introduced into the chromosome of the host strain which synthesizes the repressor protein. Transformation of the strain with a plasmid containing the repressor binding sequence results in titration of the repressor away from the biosynthetic gene, enabling expression of the essential gene.

2. Genes Essential for Cell Growth.

The repressor-titration method of the invention can be used with genes involved with the utilization of carbon sources. Specifically, the method can be used with the lactose operon and the utilization of lactose as the sole carbon source, as described herein. Other modifications will be apparent to one of skill in the art. Mutants of the lac repressor exist that are no longer able to bind the inducer (allolactose) and remain bound to the lac operator in normal inducing conditions. These are typified by the lacI$^s$ mutants; however, other mutations exist that have no capacity to bind inducer but are normal in all other functions (Chang et al., 1994, *Biochem.*, 33: 3607–3616). Strains carrying these mutations would not be able to express the genes of the lac operon and hence not be able to grow with lactose as the sole carbon source. Transformation of such strains with high copy number plasmids containing wild type lac operator sequences will titrate the repressor away from the lac operon and allow growth on lactose.

3. Genes Encoding the Synthesis of Nucleic Acids.

The invention can also be used in conjunction with essential genes encoding DNA and/or RNA synthesis or replication proteins of the host cell. Examples of such genes with respect to these essential functions in bacteria such as *E. coli* and Salmonella are known (McMacken et al., in *Escherichia coli and Salmonella typhimurium Cellular and Molecular Biology*, Eds. Neidhardt et al., Am. Soc. Micro., Wash. D.C., 1987, pp. 564–612); these include, but are not limited to, the following genes: dnaA, dnaB, dnaC, ssb, dnaG, polC (dnaE), dnaQ (mutD) dnaN, dnaZX, gyrA, gyrB, polA, lig, dnaT, rpoA, rpoB, rpoC, and rpoD.

4. Genes Encoding Antibiotic Resistance.

The invention can also be used in conjunction with antibiotic resistance. The resistance gene is constructed such that its expression is under the control of the promoter/operator that binds the desired repressor protein. This construct is then inserted into the chromosome of the host strain. Transformation of the strain with plasmid containing the repressor binding sequence will titrate the repressor from the antibiotic resistance gene and allow expression and hence growth in the presence of that antibiotic. An antibiotic resistance gene is such a useful selectable marker that a practitioner of the invention might choose antibiotic resistance as the host essential gene even though attention would have to be paid to purifying the plasmid product away from the antibiotic used in the scale-up fermentation process.

For example, the kanamycin gene can be placed under the control of the lac promoter/operator (derived from the lac sequences of pUC18), and then introduced into the chromosome of DH1. pUC4K (Pharmacia Biotech) can be used as the source of the kanamycin gene. pUC4K is then restricted with XhoI and the 5' overhang filled. This plasmid DNA is then restricted with PstI and the fragment containing the kanamycin gene is then gel purified. The XhoI restriction removes the promoter and the sequence coding for the first 10 amino acids of the kanamycin gene. pUC18 is restricted with SmaI and PstI, and the kanamycin gene is ligated into this construct. This creates an in-frame fusion between the sequence coding for the first 11 amino acids of the lacZ gene and the truncated kanamycin gene. The expression of the kanamycin gene is then placed under the control of the lac operator in the presence of the lac repressor. The construct will then be introduced into the chromosome of DH1 utilizing non-essential regions of *E. coli* DNA (see Winans et al., 1985, supra, and Jasin, 1984, supra).

In Example 1, the invention is applied using the lac repressor/operator system in experiments which demonstrate the ability plasmid borne sequences to titrate repressor away from the chromosomal gene.

b. Yeast

Host chromosome genes in yeast typically encode proteins which complement host nutritional auxotrophies. Commonly used auxotrophic markers are described above. Yeasts are resistant to tetracycline and ampicillin, but are sensitive to G418, for which the selectable marker is the neomycin resistance gene (kana), and aureobasidin A. Aureobasidin A is a cyclic depsipeptide that is toxic to yeast cells; overproduction of AUR1 (phosphatidylinositol:ceramide phosphoinositol transferase) confers resistance to this antibiotic. Plasmid-based resistance is usually achieved using the AUR1-C mutation (phe158tyr) that confers aureobasidin resistance.

Yeast cells are of use in the repressor titration system, according to the invention. In yeast, in addition to de-repression, upstream activation of gene expression is required before a TATA-box-binding protein recruits the RNA polymerase (PolII) holoenzyme complex (containing up to 50 proteins) to the TATA box and initiates transcription of mRNA (reviewed by Reece and Platt, 1997, *BioEssays*, 19(11): 1001–1010). The repressor binds a site in one of three locations: (a) in a region of up to ~400 bp between the upstream activation sequence (UAS) and the TATA box, (b) on the activator or (c) within the transcriptional machinery or chromatin components themselves. As binding of the repressor to such a site is not always sufficient to prevent transcriptional leakage of the associated essential gene, the promoter to which it is operatively linked can be partially disabled to abolish expression in the presence of bound repressor. In addition, repression can be increased by replacing weak operator O3 with operator O1 at a distance which increases the strength of the O1/Gal4P hybrid site. This distance may be 70, 92 or 115 bp. Maximum repression is achieved at 70 bp (see Müller, 1996, supra).

Figure 4:
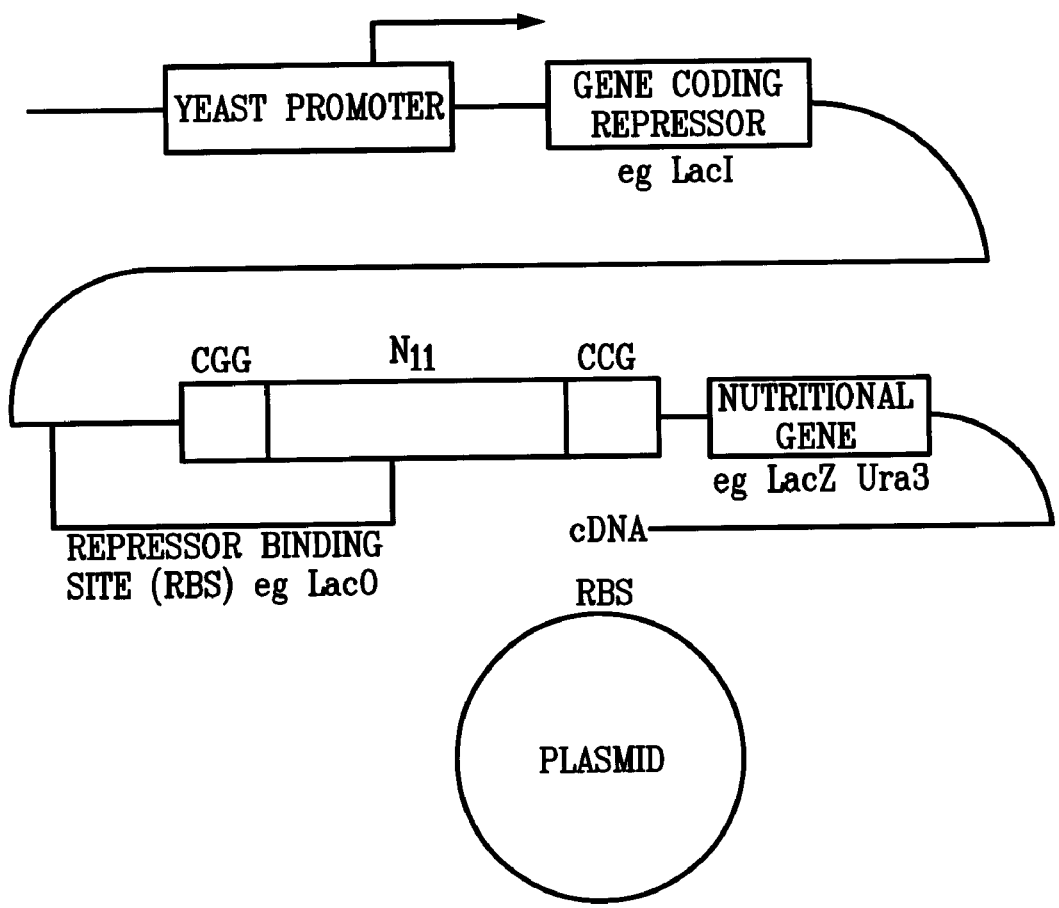
FIG. 4 is a schematic drawing of a yeast plasmid according to the invention.

For the lac repressor system to function in yeasts and be used for the maintenance of plasmids, the repressor binding site is optimally placed within the UAS controlling the essential gene. The presence of the lacI repressor bound to lacO will prevent binding of the transcriptional activator and prevent transcription. The essential gene and the gene coding for the repressor require yeast promoters for successful expression in yeasts. The lacO repressor binding site requires only cloning into the activator binding site such that it disturbs neither the activator binding consensus (CGG, any 5 bases, an A or T, any 5 bases, CCG [SEQ ID NO: 1]) nor the repressor binding sequences. An example of how this might be done is shown in FIG. 4. Competing RBS supplied on the plasmid titrates repressor away from the transcriptional activator allowing expression of the nutritional gene from a yeast promoter. A gene coding for the repressor expressed from a yeast promoter is also required in the yeast host chromosome.

An essential gene of which slight over- or underexpression does not kill the yeast cells, thereby allowing for the expression patterns of plasmid-borne genes (which are commonly observed to vary relative to those of their chromosomal counterparts), is most advantageously employed in the invention. There are about 600 essential genes in *Saccharomyces cerevisiae*. Genes encoding products which act alone (e.g., those involved in glycolysis or essential amino acid biosynthesis), rather than in large complexes, may be expected to behave in the most predictable manner, and are, therefore, advantageously used according to the invention. Examples of these such genes include, but are not limited to, the following:

ENO2 (enolase 2, or 2-phosphogycerate dehydratase, which converts 2-phospho-d-glycerate to phosphoenopyruvate in the course of glycolysis).

FBA1 (fructose-bisphosphate aldolase II, also involved in the glycolytic pathway).

THR1 (homoserine kinase, or ATP:L-homoserine-O-P-transferase, which catalyzes the first step of the threonine biosynthetic pathway).

It is also possible to use genes (e.g., ACT1 or MYO2) encoding structural proteins; however, in such cases, overexpression must be avoided, as it may be lethal or may lead to cell abnormalities.

Therapeutic Genes for Use in the Invention

Plasmid DNA produced according to the invention is useful in gene therapy when the plasmid contains a therapeutic gene. A therapeutic gene intended for in vivo expression is one which is expressible in a mammalian, preferably a human, cell and encodes RNA or a polypeptide that is of therapeutic benefit to a mammal, preferably a human. Alternatively, if such a gene is to be used in ex vivo therapy or if the product thereof is to be isolated from host cells and administered to a patient, it should be operatively linked to regulatory sequences which will direct its expression in the host cell background; in this instance, the gene should be placed and oriented such that it is not under the influence of the operator on the minimal plasmid.

Therapeutic genes useful according to the invention include, but are not limited to, those that encode proteins such as lipoproteins, glycoproteins, phosphoproteins as well as nucleic acids (e.g., RNAs such as ribozymes or antisense nucleic acids). Such genes include those encoding receptors, enzymes, ligands, regulatory factors, and structural proteins, any of which may be nuclear proteins, cytoplasmic proteins, mitochondrial proteins, secreted proteins, plasmalemma-associated proteins, serum proteins, viral antigens, bacterial antigens, protozoal antigens and parasitic antigens. Other proteins or polypeptides which may be expressed by a gene on the minimal plasmid of the invention include, but are not limited to, hormones, growth factors, neurotransmitters, enzymes, clotting factors, apolipoproteins, receptors, drugs, oncogenes, tumor antigens, tumor suppressors, structural proteins and viral antigens, parasitic antigens and bacterial antigens, which antigens can be used to induce an immunologic response, as well as other proteins of useful significance in the body.

Examples of such genes are well known in the art and include but are not limited to the β-glucocerebrosidase gene, the Bruton's thymidine kinase gene, the herpes simplex virus thymidine kinase (HSV TK) gene, genes encoding cytokines, such as TNF, interleukins 1–12, interferons (α, β, γ), $F_c$ receptor, and T-cell receptor, as well as genes encoding inhibitors of HIV, e.g., TAT or REV mutants that act as competitive inhibitors of the natural proteins. Other specific examples of therapeutic gene products include proinsulin, growth hormone, dystrophin, androgen receptors, insulin-like growth factor I, insulin-like growth factor II, insulin-like growth factor binding proteins, epidermal growth factor TGF-α, TGF-β, PDGF, angiogenesis factors (acidic fibroblast growth factor, basic fibroblast growth factor and angiogenin), matrix proteins (Type IV collagen, Type VII collagen, laminin), phenylalanine hydroxylase, tyrosine hydroxylase, oncogenes (ras, fos, myc, erb, src, sis, jun), E6 or E7 transforming sequence, p53 protein, Rb gene product, cytokine receptor, I1-1, IL-6, IL-8 and viral capsid protein.

The genes which can be incorporated into the minimal plasmid are only limited by the availability of the cloned nucleic acid sequences encoding the desired gene product. One skilled in the art will readily recognize that as more proteins and polypeptides become identified, the genes encoding them can be integrated into a minimal plasmid, as described herein, and maintained in a transfected cell by the repressor/operator titration system of the invention.

The plasmid DNA may also include marker genes, such as drug resistance genes, the β-galactosidase gene, the dihydrofolate reductase gene, and the chloramphenicol acetyl transferase gene. Use of such DNA in vivo or ex vivo where the therapeutic gene encodes a product of physiological importance, such as replacement of a defective gene or an additional potentially beneficial gene function, is expected to confer long term genetic modification of the cells and be effective in the treatment of disease. Note that while therapeutic genes typically encode proteins for which a patient might be deficient or that might be clinically-effective in higher-than-normal concentration, genes that are directed toward the elimination the of deleterious or overproduced proteins (for example, by preventing their translation) are also of use in the invention and include, but are not limited to, genes that encode antisense RNA or ribozymes. Ribozymes of the hammerhead class are the smallest known, and lend themselves both to in vitro synthesis and subsequent delivery to cells and to in vivo synthesis in a transfected cell (summarized by Sullivan, 1994, *J. Invest. Dermatol.*, 103: 85S–98S; Usman et al., 1996, *Curr. Opin. Struct. Biol.*, 6: 527–533).

Repressor Titration for In Vivo Therapy

During culturing and amplification in vitro, maintenance of plasmid DNA in bacteria is normally achieved by the incorporation of plasmid-borne DNA sequences encoding dominant selectable markers (e.g. antibiotic resistance) or auxotrophic markers (e.g., genes encoding the synthesis of essential nutrients like purine or amino acids). As stated above, the use of plasmid-borne sequences encoding dominant selectable markers (e.g. antibiotic resistance) or auxotrophic markers (e.g. genes encoding enzymes involved in the biosynthetic pathways responsible for the production of essential nutrients such as purines or amino acids) requires inclusion or omission of certain compounds from the growth medium.

Plasmids prepared according to the invention for use in in vivo therapy preferably comprise a therapeutic gene. Genes useful for therapy are described above. Following transfection and cell growth, plasmid DNA may be prepared from the host cells by methods well known in the art (see, for example, Sambrook et al., 1989, *Molecular Cloning. A Laboratory Manual 2nd Edition*, Cold Spring Harbor Laboratory Press, Cold Spring Harbor, N.Y.).

Where a gene of interest encoding a recombinant protein is carried on the plasmid such that it is under control of host cell regulatory sequences (i.e., minimally, a promoter that functions in the host cell), the recombinant protein may be produced during cell growth and then isolated according to methods known in the art, as follows. Production and purification of recombinant proteins in *E. coli* is accomplished as described in Das, 1990, "Overproduction of proteins in *E. coli*: Vectors, host and strategies", *Methods Enzymol.*, 182: 93–112; Marston et al., 1990, "Solubilization of protein aggregates", *Methods Enzymol.*, 182: 264–276; and Thatcher et al., 1994, "Protein folding in biotechnology", in Mechanisms of Protein Folding, Ed. R. H. Pain, Frontiers in Molecular Biology Series, IRL Press, Oxford University, UK.

Production and purification of soluble and/or periplasmic recombinant proteins in *E. coli* may be performed as described in Hart et al., 1994, *Bio/Technology*, 11: 1113–1117; Schein, 1989, *Bio/Technology*, 7: 1141–1149; and Lavallie et al., 1993, *Bio/Technology*, 11: 187–193.

Production and purification of recombinant proteins in *S. cerevisiae* may be performed as described in Romanos et al., 1992, "Foreign gene expression in yeast; a review", in *Yeast*, 8: 423–488.

Production and purification of recombinant proteins in yeast *Phichia pastoris* may be performed as described in Sreekrishna et al., 1989, *Biochemistry*, 28: 4117–4125.

a. Administration

Plasmid DNA containing a therapeutic gene is administered using a viral or non-viral mode of in vivo or ex vivo gene therapy. The mode of administration is not critical to the invention, and may include the use of a gene gun for administration of naked DNA, receptor-mediated gene therapy, e.g., using liposome/antibody complexes, and viral vectors.

For example, a patient that is subject to a viral or genetic disease may be treated in accordance with the invention via in vivo or ex vivo methods. For example, in in vivo treatments, plasmid DNA of the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" will be determined by the level of enhancement of function of the transferred genetic material balanced against any risk or deleterious side effects. Monitoring levels of gene introduction, gene expression and/or the presence or levels of the encoded product will assist in selecting and adjusting the dosages administered. Generally, a composition including a delivery vehicle will be administered in a single dose in the range of 10 ng–100 μg/kg body weight, preferably in the range of 100 ng–10 μg/kg body weight, such that at least one copy of the therapeutic gene is delivered to each target cell.

Repressor Titration for Ex Vivo Gene Therapy

While repressor titration may be applied to the maintenance of a plasmid in cells grown under standard in vitro culture conditions (for example, semi-solid culture medium, such as nutrient agar, or in liquid culture), the claimed invention encompasses a specialized application of the technique, in which a plasmid continues to be maintained in a transformed or transfected cell after such a cell has been administered (e.g. via transplantation) to a multicellular host, such as a mammal. It is contemplated that a gene of interest, particularly a therapeutic gene, will be expressed by the transplanted cell, thereby providing the recipient organism, particularly a human, with a needed RNA (e.g., an antisense RNA or ribozyme) or protein.

As discussed above, any cell type may be used according to the invention as a plasmid host in which a repressor has been isolated and its corresponding operator sequence determined, and for which a functional origin of replication is known which may be incorporated into a minimal plasmid. Such cells may include cells of an organism of the same species as the recipient organism, or even cells harvested from the recipient organism itself for ex vivo nucleic acid transfection prior to re-introduction. Such autologous cell transplants are known in the art. One common example is that of bone marrow transplantation, in which bone marrow is drawn either from a donor or from a clinical patient (for example, one who is about to receive a cytotoxic treatment, such as high doses of ionizing radiation), and then transplanted into the patient via injection, whereupon the cells re-colonize bones and other organs of the hematopoietic system.

a. Dosage

Cells

Note that the present invention, as regards the transplantation of cells comprising stably-maintained plasmids into a recipient individual, is directed at a method of efficient gene transfer; therefore, the number of transfected cells which are administered to a recipient organism is determined by dividing the absolute amount of therapeutic or other gene product required by the organism by the average amount of such an agent which is produced by a transfected cell. Note that steady-state plasmid copy number varies depending on the strength of its origin of replication as well as factors determined by the host cell environment, such as the amount of repressor to be titrated and the availability of nucleotides and replicative enzyme complexes, as does the level of expression of the gene of interest encompassed by the plasmid, which level likewise is determined by the strength of its associated promoter and the availability of nucleotides and transcription factors in a given host cell background. As a result, the level of expression per cell of a given gene of interest must be determined empirically prior to administration of cells to a recipient.

While the invention provides a means by which a plasmid is stably-maintained in a transfected cell, upon which it confers a growth advantage over comparable cells which are untransfected, it does not ensure that the transfected cell is by any means immortal. In addition, the requirements of the recipient organism for the product encoded by the transgene may change over time. In light of these considerations, it is contemplated that cells of the invention may be administered in a single dose or in multiple doses, as needed. A multiple dose schedule is one in which a primary course of administration can include 1–10 separate doses, followed by other doses given at subsequent time intervals required to maintain and or reinforce the cellular level of the transfected nucleic acid. Such intervals are dependent on the continued need of the recipient for the therapeutic gene product. Preferably, when the medical needs of the recipient mammal dictate that a gene product will be required throughout its lifetime, or at least over an extended period of time, such as a year or more, the transfected cells will be replenished on a regular schedule, such as monthly or semi-monthly.

Nucleic acid

The absolute amount of minimal plasmid which is transfected into cells prior to transplantation is not critical, since a) in cells receiving at least one copy of the plasmid, it will replicate until an equilibrium copy-number is achieved, which number is correlates positively with the amount of repressor to be titrated out in the cells and the affinity of the operator for the repressor, as well as the strength of the origin of replication of the plasmid, and b) cells not receiving a copy of the plasmid will be selected out of the population according to the invention. As a first approximation, an amount of plasmid equivalent to between 1 and 10 copies thereof per cell to be transfected may be used; one of skill in the art may adjust the ratio of plasmid molecules to cells as is necessary to optimize plasmid uptake. In order to ensure that the cells which are to be transplanted into the recipient organism have received the plasmid, they must be cultured for a time (at least two, and preferably three or more generations) in vitro after transfection and prior to transplantation.

b. Administration

Autologous or Syngeneic Cells

A cell type which is commonly transplanted between individuals of a single species (or, even, from an individual to a cell culture system and back to the same individual) is that of hematopoietic stem cells (HSCs), which are found in bone marrow; such cells have the advantage that they are amenable to nucleic acid transfection while in culture, and are, therefore, well suited for use in the invention. Cultures of HSCs are transfected with a minimal plasmid comprising an operator sequence and a gene of interest and the transfected cells administered to a recipient mammal in need of the product of this gene. Transfection of hematopoietic stem cells is described in Mannion-Henderson et al., 1995, *Exp. Hematol.*, 23: 1628; Schiffmann et al., 1995, *Blood*, 86: 1218; Williams, 1990, *Bone Marrow Transplant*, 5: 141; Boggs, 1990, *Int. J. Cell Cloning*, 8: 80; Martensson et al., 1987, *Eur. J. Immunol.*, 17: 1499; Okabe et al., 1992, *Eur. J. Immunol*, 22: 37–43; and Baneri et al., 1983, *Cell*, 33: 729. Such methods may advantageously be used according to the present invention. Administration of transfected cells proceeds according to methods established for that of non-transfected cells, as described below.

The transplantation of hematopoietic cells, such as in a bone marrow transplant, is commonly performed in the art by procedures such as those described by Thomas et al. (1975, *New England J. Med.*, 292: 832–843) and modifications thereof. Such a procedure is briefly summarized: In the case of a syngeneic graft or of a patient suffering from an immunological deficiency, no immunosuppressive pre-treatment regiment is required; however, in cases in which a cells of a non-self donor are to be administered to a patient with a responsive immune system, an immunosuppressive drug must be administered, e.g. cyclophosphamide (50 mg/kg body weight on each of four days, with the last does followed 36 hours later by the transplant). Leukemic patients routinely receive a 1000-rad midline dose of total-body irradiation in order to ablate cancerous blood cells; this irradiation also has an immune-suppressive effect. Following pre-treatment, bone marrow cells (which population comprises a small number of pluripotent hematopoietic stem cells, or HSCs), are administered via injection, after which point they colonize the hematopoietic system of the recipient host. Success of the graft is measured by monitoring the re-appearance of the numerous adult blood cell types by the immunological and molecular methods which are well known in the art. While as few as 1–10 HSCs are, in theory, able to colonize and repopulate a lethally-irradiated recipient mammal over time, it is advantageous to optimize the rate at which repopulation occurs in a human bone marrow transplant patient; therefore, a transplanted bone marrow sample comprising 10 to 100, or even 100 to 1000 HSCs should be administered in order to be therapeutically effective.

Xenogeneic Cells

While transfection and subsequent tranplantation of cells which are obtained from an individual or cell culture system of like species with the recipient organism, it is more typically true that the invention is most conveniently practised using cells of another organism (such as a well-characterized microorganism, e.g. yeast, in which repressor/operator pairs and useful origins of replication are known). In such a case, certain concerns must be addressed.

First, when a protein is encoded by the gene of interest, the transplanted cells must produce the protein in a form that may is of use to the recipient organism. Post-translational processing (including, but not limited to, cleavage and patterns of glycosylation) must be consistent with proper function in the recipient. In addition, either a protein or an RNA molecule of interest must be made available to the recipient after synthesis, such as by secretion, excretion or exocytosis from the transplanted cell. To address the former, the protein produced by the transfected cells may be qualitatively compared to the native protein produced by an individual of the same species as the recipient organism by biochemical methods well known in the art of protein chemistry. The latter, release of the protein of interest by the cells to be transplanted, may be assayed by isolating protein from culture medium which has been decanted from the transfected cells or from which such cells have been separated (i.e. by centriftigation or filtration), and performing Western analysis using an antibody directed at the protein of interest. Antibodies against many proteins are commercially available; techniques for the production of antibody molecules are well known in the art.

Second, the cells must be shielded from immune rejection by the recipient organism. Methods for the encapsulation of living cultures of cells for growth either in an artificial growth environment, such as in a fermentor, or in a recipient organism have been developed, and are of use in the administration of cells transfected according to the invention. Such an encapsulation system renders the cell invisible to immune detection and, in addition, allows for the free exchange of materials (e.g. the gene product of interest, oxygen, nutrients and waste materials) between the transplanted cells and the environment of the host organism. In the Salmonella nucleic acid delivery system described above (Pawalek et al., 1997, supra), no such shielding is employed, as it is intended that the plasmid host cells infiltrate the target tissue and, preferably, cells thereof.

Methods and devices for cell encapsulation are disclosed in numerous U.S. Patents; among these are U.S. Pat. Nos. 4,353,888; 4,409,311; 4,673,566; 4,744,933; 4,798,786; 4,803,168; 4,892,538; 5,011,472; 5,158,881; 5,182,111; 5,283,187; 5,474,547; 5,498,401 (which is particularly directed to the encapsulation of bacterial and yeast cells in chitosan); U.S. Pat. Nos. 5,550,050; 5,573,934; 5,578,314; 5,620,883; 5,626,561; 5,653,687; 5,686,115; 5,693,513; and 5,698,413, the contents of which are fully incorporated by reference herein. Typically required for the successful culture of encapsulated cells is a selectively-permeable outer covering or 'skin' which is biocompatible (i.e., tolerated by both the encapsulated cells and the recipient host), and, optionally, a matrix in- or upon which cells are distributed such that the matrix provides structural support and a substrate to which anchorage-dependent cells may attach themselves. As relates to encapsulation devices applicable to use in the invention, the term "selectively-permeable" refers to materials comprising openings through which small molecules (including molecules of up to about 50,000 M.W.–100,000 M.W.) may pass, but from which larger molecules, such as antibodies (approximately 150,000 M.W.), are excluded. Suitable covering materials include, but are not limited to, porous and/or polymeric materials such as polyaspartate, polyglutamate, polyacrylates (e.g., acrylic copolymers or RL®, Monsanto Corporation), poly-vinylidene fluoride, polyvinylidienes, polyvinyl chloride, polyurethanes, polyurethane isocyanates, polystyrenes, polyamides, cellulose-based polymers (e.g. cellulose acetates and cellulose nitrates), polymethyl-acrylate, polyalginate, polysulfones, polyvinyl alcohols, polyethylene oxide, polyacrylonitriles and derivatives, copolymers and/or mixtures thereof, stretched polytetrafluoroethylene (U.S. Pat. Nos. 3,953,566 and 4,187,390, both incorporated herein by reference), stretched polypropylene, stretched polyethylene, porous polyvinylidene fluoride, woven or non-woven collections of fibers or yarns, such as "Angel Hair" (Anderson, *Science*, 246: 747–749; Thompson et al., 1989, *Proc. Natl. Acad. Sci. U.S.A.*, 86: 7928–7932), fibrous matrices (see U.S. Pat. No. 5,387,237, incorporated herein by reference), either alone or in combination, or silicon-oxygen-silicon matrices (U.S. Pat. No. 5,693,513). Polylysine having a molecular weight of 10,000 to 30,000, preferably 15,000 to 25,000 and most preferably 17,000 is also of use in the invention (see U.S. Pat. No. 4,673,566). Alternatively, the matrix material, comprising the transfected cells of the invention, is exposed to conditions that induce it to form its own outer covering, as discussed below. As described in U.S. Pat. No. 5,626,561, the selective permeability of such a covering may be varied by impregnating the void spaces of a porous polymeric material (e.g., stretched polytetrafluoroethylene) with a hydrogel material. Hydrogel material can be impregnated in substantially all of the void spaces of a porous plymeric material or in only a portion of the void spaces. For example, by impregnating a porous polymeric material with a hydrogel material in a continuous band within the material adjacent to and/or along the interior surface of a porous polymeric material, the selective permeability of the material is varied sharply from an outer cross-sectional area of the material to an inner cross-sectional area of the material. The amount and composition of hydrogel material impregnated in a porous polyhmeric material depends in large part on the particular porous polymeric material used to encapsulate cells for transplant. Examples of suitable hydrogel materials include, but are not limited to, HYPAN® Structural Hydrogel (Hymedix International, Inc.; Dayton, N.J.), non-fibrogenic alginate, as taught by Dorian in PCT/US93/05461, which is incorporated herein by reference, agarose, alginic acid, carrageenan, collagen, gelatin, polyvinyl alcohol, poly(2-hydroxyethyl methacrylate), poly(N-vinyl-2-pyrrolidone) or gellan gum, either alone or in combination.

The matrix typically has a high surface-area:volume ratio, comprising pores or other spaces in- or on which cells may grow and through which fluids may pass; in addition, suitable matrix materials are stable following transplantation into a recipient organism. Preferably, the matrix comprises an aggregation of multiple particles, fibers or laminae. Alternatively, a matrix may comprise an aqueous solution, such as a physiological buffer or body fluid from the recipient organism (see U.S. Pat. No. 5,011,472). Suitable matrix materials include liquid, gelled, polymeric, co-polymeric or particulate formulations of aminated glucopolysachharides (e.g., deacetylated chitin, or "chitosan", which is prepared from the pulverized shells of crabs or other crustaceans, and is commercially available as a dry powder; Cat. # C 3646, Sigma, St. Louis, Mo.), alginate (U.S. Pat. No. 4,409,331), poly-$\beta$-1$\rightarrow$5-N-acetylglucosamine (p-GlcNAc) polysaccharide species (either alone of formulated as co-polymer with collagen; see U.S. Pat. No. 5,686,115), reconstituted extracellular matrix preparations (e.g. Matrigel®; Collaborative Research, Inc, Lexington, Mass.; Babensee et al., 1992, *J. Biomed. Matr. Res.*, 26: 1401), proteins, polyacrylamide, agarose and others.

Methods by which cells become encapsulated using such materials are both numerous and varied. Encapsulation devices comprising a semi-permeable membrane material, as described above, may be pre-formed, filled with cells (e.g. by injection or other manual means) and then sealed (U.S. Pat. Nos. 4,892,538; 5,011,472; 5,626,56; and 5,653,687); such sealing may be effectively permanent (e.g. by the use of heat-sealing), semi-permanent (e.g. by the use of a biocompatible adhesive, such as an epoxy, which will not dissolve or degrade in an aqueous environment) or temporary (e.g. by the use of a removable cap or plug, or by shutting of a valve or stopcock). Methods of permanent and semi-permanent sealing are disclosed in U.S. Pat. No. 5,653,687. As an alternative to the use of a pre-formed, semi-permeable cell reservoir, methods by which cells suspended in matrix material and the substance which is to form the outer covering of the encapsulation device are co-extruded under conditions which cause the cell/matrix mixture, which may be in liquid or semi-liquid (i.e., gelled) form to be encased in a continuous tube of the semi-permeable polymer, which either forms, or becomes crosslinked, under the extrusion conditions; such an extrusion procedure may lead to the formation of capsules which have only one cell reservoir (U.S. Pat. No. 5,283,187) or which are divided into multiple, discrete compartments (U.S. Pat. No. 5,158,881). As an alternative to both types of procedure, a liquid or semi-liquid (i.e., gelled) cell/matrix mixture droplet is suspended either in an agent which induces 'curing' or crosslinking of the outer layer of matrix material to form a semi-permeable barrier (U.S. Pat. Nos. 4,798,786 and 5,489,401) or in a solution of polymeric material (or monomers thereof), which will polymerize and/or crosslink upon contact with the cell/matrix droplet such that a semi-permeable membrane is deposited thereon (U.S. Pat. Nos. 4,353,888; 4,673,566; 4,744,933; 5,620,883; and 5,693,513).

One of skill in the art is well able to select the appropriate matrix and semi-permeable membrane materials and to construct a cell-encapsulation device as described above.

Implantation of such a device is achieved surgically, via standard techniques, to a site at or near the anatomical location to which the product encoded by the gene on the minimal plasmid of the invention is to be delivered, as is deemed safest and most expedient. Such a device may take any convenient shape, including, but not limited to, that of a sphere, pellet or other capsule shape, disk, rod or tube; often, the shape of the device is determined by its method of synthesis. For example, one which is formed by co-extrusion of a cell suspension and a polymeric covering material is typically tubular, while one formed by the deposition of a covering on droplets comprising cells in matrix material might be spherical. As discussed above, the number of cells which must be implanted (and, therefore, encapsulated) is dependent upon the requirements of the recipient organism for the product of the transfected gene. The encapsulation devices described above are typically small (most usefully, 10 $\mu$m to 1 $\mu$m in diameter, so as to permit efficient diffusion of substances back and forth between the outer covering and the cells most deeply embedded in the matrix), and it is contemplated that such devices may carry between 10 and $10^{10}$ cells each. Should the need for larger numbers of cells be anticipated, a plurality (2, 10 or even 100 or more) of such in vivo culturing devices may be made and implanted in a given recipient organism.

An encapsulated cell device may be intended for permanent installation; alternatively, retrieval of the device may be desirable, whether to terminate delivery of the product of the transgene to the recipient organism at the discretion of one of skill in the art, such as a physician (who must determine on a case-by-case basis the length of time for which a given cell implant is beneficial to the recipient organism) or to replenish the device with fresh cells after long-term use (i.e. months to years). To the latter end, an implantation device may usefully comprise a retrieval aid, such as a guidewire, and a cap or other port, such as may be opened and re-sealed in order to gain access to the cell reservoir, both as described in U.S. Pat. No. 4,892,538.

Live cultures of encapsulated cells have been used successfully to deliver gene products to tissues of a recipient animal. U.S. Pat. No. 4,673,566 discloses successful maintenance of normal blood sugar levels in a diabetic rat into which encapsulated rat islet of Langerhans cells were implanted; two administrations of 3,000 cells each together were effective for six months, while a single dose of 1,000 cells was effective for two months.

Encapsulated GABA-secreting pancreatic cells implanted into subthalamic nucleus of monkeys in whom Parkinsonism has been clinically-induced have been observed relieve the symptoms of that syndrome (U.S. Pat. No. 5,474,547), demonstrating invisibility of encapsulated cells to the immune system, as well as efficacy in delivering a product of encapsulated, transplanted cells to a recipient organism.

More encouraging, as it demonstrates immunological shielding by cell encapsulation systems sufficient for cross-species cell transplants, as is advantageous for their use in practicing the present invention, is the finding that encapsulated embryonic mouse mesencephalon cells, when transplanted into recipient rats, alleviate symptoms of clinically-induced Parkinsonism (U.S. Pat. No. 4,892,538).

Similarly, heterospecific transplantation of encapsulated islet cells has been demonstrated to treat diabetes successfully (dog islet cells to a mouse recipient, U.S. Pat. No. 5,578,314; porcine islet cells to a mouse recipient, Sun et al., 1992, *ASAIO J.*, 38: 124). It is believed that such an approach is promising for the clinical treatment of diabetes mellitus in humans (Calafiore, 1992, *ASAIO J.*, 38: 34).

It is contemplated that these techniques, which have been applied successfully to untransfected cells, may be utilized advantageously with cells that are transfected with stably-maintained plasmids of the invention.

c. Assay of Efficacy of Transplanted Cells in a Recipient Organism

The efficacy of the transfected cells so administered and their subsequent maintenance in the recipient host may be assayed either by monitoring the activity of a marker gene, which may additionally be comprised by the transfected construct, or by the direct measurement of either the product (e.g. a protein) encoded by the gene of interest or the reduction in the levels of a protein the production of which it (an antisense message or ribozyme) is designed to inhibit. The assays can be performed using conventional molecular and biochemical techniques, such as are known to one skilled in the art.

In addition to direct measurements of protein or nucleic acid levels in blood or target tissues encoded by the transfected gene borne by the minimal plasmid in transfected/transplanted cells, it is possible to monitor changes in the disease state in patients receiving gene transfer via transplantation of cells in which the plasmid is stably-maintained by the repressor/operator titration system of the invention and compare them to the progression or persistence of disease in patients receiving comparable cells transfected by conventional means.

EXAMPLE 1

E. coli strain DH1 (Hanahan, 1983, J. Mol. Biol., 166: 557–580) possesses an intact lactose operon which is subject to control by the lactose repressor protein (LacI). LacI is present at 10–20 copies per cell and binds with high affinity ($k_d 1 \times 10^{-14}$). DH1 cells were transformed with pUC18tet (a pUC18-based plasmid containing ampicillin and tetracycline resistance genes that is present at approximately 100–200 copies per cell). pUC18tet contains the lac operator/promoter but does not contain LacI gene encoding the repressor protein. The plasmid also contains the pUC origin of replication and a polylinker (or multiple cloning site) for insertion of a therapeutic gene. Plasmid-encoded ampicillin and tetracycline resistance is not necessary for repressor titration, and a plasmid containing no antibiotic resistance is preferred according to the invention, and may be readily substituted for pUC18tet.

DH1 and DH1: :pUC18tet were grown on M9 minimal salts medium with lactose (10 mM) or glucose (10 mM) as carbon sources supplemented with ampicillin (50 µg/ml) where necessary. Cells were harvested during log growth and assayed for β-galactosidase activity (Miller, 1972, Experiments in Molecular Genetic, Cold Spring Harbor Laboratory, CSH, N.Y.). As shown in Table 1, comparable β-galactosidase activities were observed with DH1::pUC18tet grown on glucose and lactose, whereas very much lower activities were seen with DH1 grown on glucose compared to those grown on lactose. The presence of the plasmid, therefore, titrates the lac repressor away from the lac operon, allowing the expression of β-galactosidase.

TABLE 1

Expression of β-galactosidase in E. coli DH1 in the presence and absence of pUC18tet when grown under inducing and non-inducing conditions

|  | DH1 Activity (units) | % | DH1::pUC18tet Activity (units) | % |
|---|---|---|---|---|
| Experiment 1 |  |  |  |  |
| Lactose | 1391 | 100 | 4162 | 300 |
| Glucose | 27 | 2 | 3120 | 224 |
| Experiment 2 |  |  |  |  |
| Lactose | 2571 | 100 | 7140 | 277 |
| Glucose | 9 | 0 | 6466 | 255 |
| Experiment 3 |  |  |  |  |
| Lactose | 1123 | 100 | 1400 | 125 |
| Glucose | 29 | 2.5 | 1157 | 103 |

Results are of three independent experiments and are expressed as units and as a percentage of value obtained for lactose grown DH1 for each experiment.

EXAMPLE 2

Plasmid DNA stably maintained in a host cell according to the invention is isolated as follows. Cells are lysed and plasmid DNA purified according to methods well known in the art, and as described in (see Birnboim et al., 1979., Nucleic Acids Res., 7: 1513–1523, and Birnboim, 1983, Methods Enzymol., 100: 243–255) or using a commercially-available plasmid preparation kit, e.g. a Qiagen plasmid mini, maxi, or mega kit (Qiagen; Chatsworth, Calif.). For large-scale purification of plasmid DNA, e.g., 100 mg or greater, is also possible (see Horn et al., 1995, Human Gene Therapy, 6: 565–573).

EXAMPLE 3

The Repressor Titration System in the Treatment of X-linked γ-globulinemia

Both in vivo and ex vivo treatment are contemplated within the present invention. Accordingly, a plasmid maintained by the repressor titration system or a therapeutic gene product encoded by such a plasmid may be prepared and administered to a patient, as described above. Similarly, cells are removed from the patient or otherwise provided, transduced with a plasmid containing a therapeutic gene in accordance with the invention, then reintroduced into the patient, also by methods such as those described above. Any of the useful cell types disclosed above are used in the practise of either in vivo or ex vivo therapy according to the invention.

Two representative plasmids are described below for treatment of human genetic diseases. A plasmid according to the invention is constructed to treat X-linked γ-globulinemia. This plasmid comprises the minimal sequences described herein, i.e., an origin of replication for replication in a bacterial or yeast host cell, an operator sequence, and a site for insertion of a therapeutic gene. For example, the pUC18tet plasmid is used as a minimal plasmid, preferably with the tet gene deleted. A therapeutic gene, such as the Bruton's kinase gene (Vetrie et al., 1993, Nature, 361: 226–233), is carried on DNA fragments described below, which are spliced together using recombinant DNA procedures well-known in the art. The Bruton's Tyrosine Kinase human gene is carried on a 2.1 kb fragment delineated by the PvuI site at position (+33) and the HindIII site at position (+2126). Optionally, the plasmid also includes sequences which confer position independent, tissue specific gene expression, as taught in PCT/GB88/00655, as well as a sequences encoding a splice site and polyadenlyation signal operatively linked to the therapeutic gene, which sequences may include portions of the human β globin locus splice and poly A signals (i.e., a BamHI-XbaI 2.8 kb 3' splice/poly-A flanking sequence containing exon 2 —IVSII—exon 3—polyA sequences).

Plasmid DNA is prepared as described herein above and used to treat X-linked γ-globulinemia by introducing the construct directly into a patient for in vivo gene therapy or into pre-B cells for ex vivo therapy, as described above and in Martensson et al., Eur. Jour. Immunol., 1987, 17: 1499; Okabe et al., 1992, Eur. Jour. Immunol., 22: 37; and Baneiji et al., 1983, Cell, 33: 729, and administering the transfected pre-B cells into a patient afflicted with X-linked γ-globulinemia, also as described above.

The progression of known clinical indicators is monitored, wherein improvement in such an indicator (e.g. an increase in serum levels of γ-globulin or a decreased severity of disease-associated symptoms) is indicative of efficacy of treatment according to the invention.

EXAMPLE 4

The Repressor Titration System in the Treatment of Gaucher's Disease

Plasmid DNA is prepared according to the invention for the treatment of Gaucher's disease. Gaucher's disease stems from one of two different genetic mutations. Gaucher's type 1 is a CGG→CAG mutation, which results in an Arg→Gln substitution at position 119 of the β-glucocerebrosidase polypeptide (Graves, 1988, DNA, 7: 521). Gaucher's type 2 is a CTG→CCG mutation, which results in a Leu→Pro substitution at position 444 of the β-glucocerebrosidase polypeptide (Tsuji, 1987, New England J. Med., 316: 570). The presence of a β-glucocerebrosidase gene encoding a wild type polypeptide is believed to substantially correct Gaucher's disease. Therefore, the therapeutic plasmid contains the minimal elements described herein (i.e., an origin of replication, an operator sequence, and a cloning site) and the lysozyme gene promoter operatively linked to the β-glucocerebrosidase transgene, as described in Horowitz et al., 1989, *Genomics.*, 4: 87–96. This plasmid is constructed as follows:

The human β-glucocerebrosidase gene is carried (as disclosed in Horowitz et al., 1989, supra) on a 9722 base pair fragment extending from a BamHI site in exon 1 to an EcoRV site 3' to polyadenylation site. This fragment contains 11 exons and all intervening sequences, with translational start site in exon 2.

Once constructed, the plasmid is transfected into an appropriate host cell strain, such as any of those listed avove; following cell culture, plasmid DNA is prepared as described herein and is then used to treat Gaucher's disease by introducing the DNA directly into the host for in vivo treatment. Alternatively, the plasmid DNA is transfected into macrophages for ex vivo therapy (see *Immunology and Cell Biology*, 1993, Vol. 71, pages 75–78) and the transfected macrophages are subsequently administered to a patient afflicted with Gaucher's disease by transplantation methods known in the art, such as those described above.

Expression of the wild-type transgene in the patient so treated is assayed by any of a number of methods known in the art, such as measurement of wild-type β-glucocerebrosidase levels, e.g. by immunological staining of two-dimensional SDS/polyacrylamide gels bearing samples of proteins derived from the patient before and after treatment according to the invention. Efficacy of the transgene in the treatment of Gaucher's disease is assessed by one skilled in the art, such as a physician, by monitoring changes in disease-associated indicators in a patient so afflicted following treatment.

EXAMPLE 5

Stable Maintenance of a Plasmid in Yeast

Figure 5:
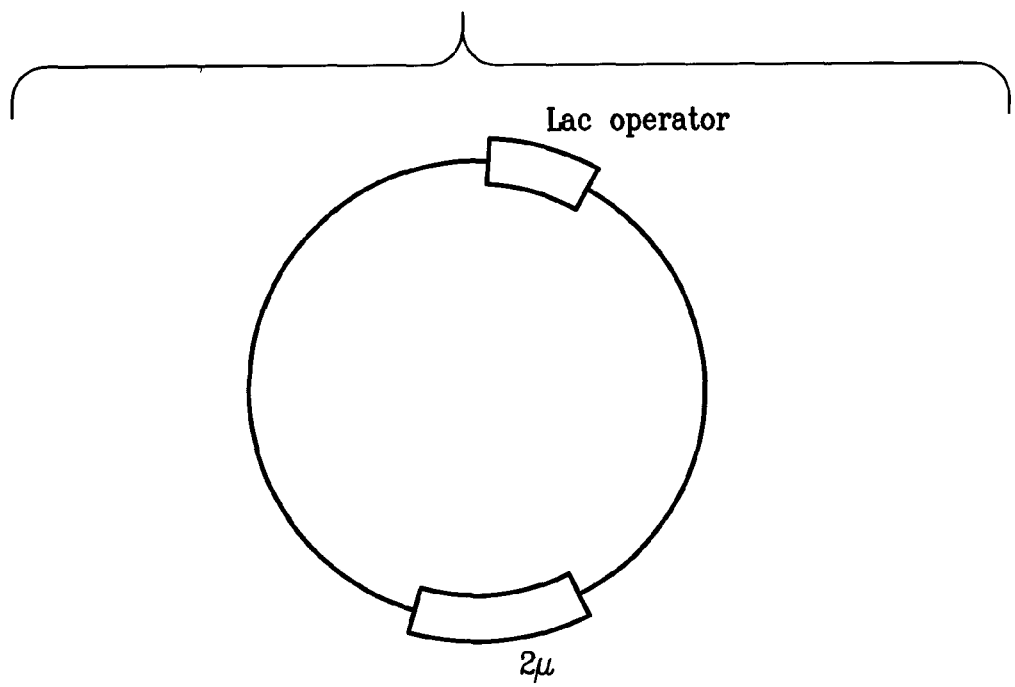
FIG. 5 is a schematic representation of repressor titration in yeast.
Figure 5:
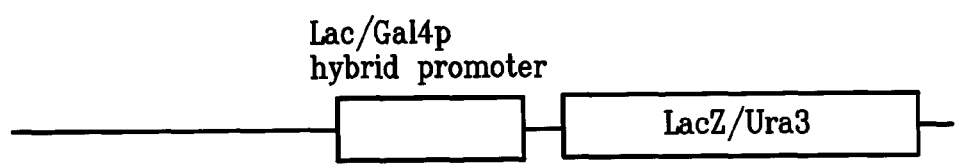
Figure 5:
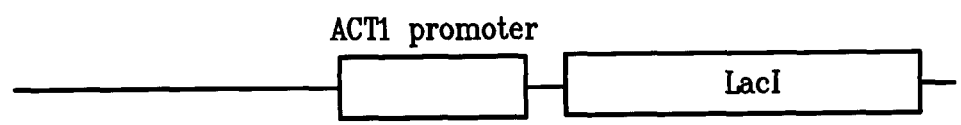

The hybrid LacI/Gal4p binding site described above is cloned into a plasmid containing a promoter-disabled version of LacZ (for the purposes of testing the repressor titration system) or a yeast gene required for growth on a particular media, (e.g., Ura3). A version of LacI under the control of a constitutive yeast promoter, such as ACT1, is integrated into the yeast genome so that the yeast cells express the Lac repressor. The repressor binds to the hybrid promoter and prevents Gal4p binding. Thus, the gene is inactive, as judged by either white color in X-GAL containing plates (LacZ reporter) or the inability to grow on media lacking uracil (Ura3 reporter). A plasmid is then introduced into this yeast strain bearing a yeast origin of replication and one or more Lac operator sites, which sites will compete LacI from the hybrid promoter, thereby allowing Gal4p to bind that element. The transformed yeast cells are then plated onto a medium lacking uracil to select for Ura$^+$cells which are subsequently screened for blue color on a culture plates containing X-GAL. This two-tiered selection enables correct analysis without the identification of false positives (cells which display promiscuous transcription of the essential gene in the absence of the operator-bearing plasmid) using either selection method singly. Transcription is activated in the presence of the plasmid, as indicated by yeast which survive on media lacking uracil or which score blue on X-GAL-containing plates. The scheme is shown diagrammatically in FIG. 5.

USE

The invention is useful for the stable maintenance of transfected, extrachromosomal nucleic acid molecules in a host cell over many generations of culturing in the absence of extracellular selective conditions (for example, nutrient deprivation or the presence of a selective substance, e.g. an antibiotic). The invention is additionally useful for the preparation of a product of a transfected gene which is free of contamination by selective agents, e.g. antibiotics. The invention is additionally useful as a means to deliver a stably-maintained plasmid to a recipient organism. Lastly, the invention is useful for administering a therapeutic gene to a recipient organism in need thereof.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

---

What is claimed is:

1. A method of delivering a stably maintained plasmid to a recipient organism comprising the steps of:
   a) culturing a host cell comprising:
      (i) a chromosomal gene essential for cell growth that is functionally associated with an operator susceptible to binding by a repressor produced by a second chromosomal gene, and
      (ii) a plasmid comprising an operator susceptible to binding by said repressor, wherein said repressor represses transcription of said chromosomal gene essential for cell growth in the absence of said plasmid, thereby inhibiting cell growth and wherein, when said plasmid is present in cells in sufficient numbers to titrate said repressor, said chromosomal gene essential for cell growth is expressed, thereby conferring a growth advantage on said cell;
   b) selecting cells containing the plasmid based upon cell growth; and
   c) transplanting said selected cells to said recipient organism.

2. A method of delivering a stably maintained plasmid to a recipient organism comprising the steps of:
   a) culturing a host cell comprising:
      (i) an exogenous chromosomal gene essential for cell growth under certain conditions that is functionally associated with an operator susceptible to binding by a repressor produced by a second chromosomal gene, and
      (ii) a plasmid comprising an operator susceptible to binding by said repressor, wherein said repressor represses transcription of said exogenous chromosomal gene in the absence of said plasmid;
   b) selecting cells containing the plasmid based upon cell growth, under conditions in which said exogenous chromosomal gene is essential; and
   c) transplanting said selected cells to said recipient organism.

3. A method of maintaining a host cell containing a gene of interest in a host organism, comprising the steps of:
   a) culturing a host cell comprising:
      (i) a chromosomal gene essential for cell growth that is functionally associated with an operator susceptible to binding by a repressor produced by a second chromosomal gene, and
      (ii) a plasmid comprising an operator susceptible to binding by said repressor and said gene of interest which is expressed in said cell,
      wherein said repressor represses transcription of said chromosomal gene essential for cell growth in the absence of said plasmid, thereby inhibiting cell growth and wherein, when said plasmid is present in cells in sufficient numbers to titrate said repressor, said chromosomal gene essential for cell growth is expressed, thereby conferring a growth advantage on said cell;
   b) selecting cells containing the plasmid based upon cell growth; and
   c) transplanting said selected cells to said recipient organism, wherein said chromosomal gene is essential for cell growth in said recipient organism.

4. A method of maintaining a host cell containing a gene of interest in a host organism, comprising the steps of:
   a) culturing a host cell comprising:
      (i) an exogenous chromosomal gene essential for cell growth under certain conditions that is functionally associated with an operator susceptible to binding by a repressor produced by a second chromosomal gene, and
      (ii) a plasmid comprising an operator susceptible to binding by said repressor and said gene of interest which is expressed in said cell,
      wherein said repressor represses transcription of said exogenous chromosomal gene in the absence of said plasmid;
   b) selecting cells containing the plasmid based upon cell growth, under conditions in which said exogenous chromosomal gene is essential; and
   c) transplanting said selected cells to said recipient organism, wherein said plasmid is maintained in said selected cells in said recipient organism under said certain conditions.

5. A method of delivering a stably maintained plasmid to a recipient organism comprising the steps of:
   a) culturing a host cell comprising:
      (i) an exogenous chromosomal gene essential for cell growth that is functionally associated with an operator susceptible to binding by a repressor produced by a second chromosomal gene, wherein said exogenous chromosomal gene replaces an endogenous chromosomal gene essential for cell growth that has been deleted from said host cell, and wherein all functional copies of the chromosomal gene essential for cell growth are functionally associated with an operator susceptible to binding by said repressor and
      (ii) a plasmid comprising an operator susceptible to binding by said repressor, wherein said repressor represses transcription of said exogenous chromosomal gene in the absence of said plasmid;
   b) selecting cells containing the plasmid based upon cell growth; and
   c) transplanting said selected cells to said recipient organism.

6. A method of maintaining a host cell containing a gene of interest in a host organism, comprising the steps of:
   a) culturing a host cell comprising:
      (i) an exogenous chromosomal gene essential for cell growth that is functionally associated with an operator susceptible to binding by a repressor produced by a second chromosomal gene, wherein said exogenous chromosomal gene replaces an endogenous chromosomal gene essential for cell growth that has been deleted from said host cell, and wherein all functional copies of the chromosomal gene essential for cell growth are functionally associated with an operator susceptible to binding by said repressor, and
      (ii) a plasmid comprising an operator susceptible to binding by said repressor and said gene of interest,
   wherein said repressor represses transcription of said exogenous chromosomal gene in the absence of said plasmid;
   b) selected cells containing the plasmid based upon cell growth; and
   c) transplanting said selected cells to said recipient organism, wherein said exogenous chromosomal gene is essential for growth in said recipient organism.

7. The method of claim 1, 2, or 5, wherein said transplanting comprises injection of said cells into said recipient organism.

* * * * *